(12) United States Patent
Murayama et al.

(10) Patent No.: US 9,463,462 B2
(45) Date of Patent: Oct. 11, 2016

(54) NUCLEIC ACID AMPLIFICATION REACTION APPARATUS AND NUCLEIC ACID AMPLIFYING METHOD

(71) Applicant: Seiko Epson Corporation, Tokyo (JP)

(72) Inventors: Toshiro Murayama, Fujimi (JP); Atsushi Oshima, Kanie (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 14/337,527

(22) Filed: Jul. 22, 2014

(65) Prior Publication Data

US 2015/0031036 A1    Jan. 29, 2015

(30) Foreign Application Priority Data

Jul. 29, 2013  (JP) ................................. 2013-156422

(51) Int. Cl.
*C12Q 1/68* (2006.01)
*C12P 19/34* (2006.01)
*B01L 7/00* (2006.01)
*G01N 21/64* (2006.01)
*B01L 3/00* (2006.01)

(52) U.S. Cl.
CPC .............. *B01L 7/525* (2013.01); *B01L 3/502* (2013.01); *C12Q 1/686* (2013.01); *G01N 21/645* (2013.01); *B01L 2200/025* (2013.01); *B01L 2200/0647* (2013.01); *B01L 2200/0673* (2013.01); *B01L 2200/10* (2013.01); *B01L 2300/0654* (2013.01); *B01L 2300/0832* (2013.01); *B01L 2300/0838* (2013.01); *B01L 2300/1805* (2013.01); *B01L 2400/043* (2013.01); *B01L 2400/0409* (2013.01); *B01L 2400/0478* (2013.01)

(58) Field of Classification Search
None
See application file for complete search history.

(56) References Cited

U.S. PATENT DOCUMENTS

| 6,515,743 B1* | 2/2003 | Hayashi | G01N 21/6452 250/458.1 |
|---|---|---|---|
| 2010/0285989 A1* | 11/2010 | Huo | C12Q 1/682 506/9 |
| 2012/0225001 A1 | 9/2012 | Koeda | |
| 2013/0157276 A1* | 6/2013 | Edvinsson | B01L 7/52 435/6.12 |
| 2013/0210081 A1 | 8/2013 | Koeda | |

FOREIGN PATENT DOCUMENTS

| JP | 2009-136250 A | 6/2009 |
| JP | 2012-115208 A | 6/2012 |
| JP | 2012-179002 A | 9/2012 |

* cited by examiner

*Primary Examiner* — Young J Kim
(74) *Attorney, Agent, or Firm* — Harness, Dickey & Pierce, P.L.C.

(57) ABSTRACT

A nucleic acid amplification reaction apparatus includes (A) a rotating body mounted with a nucleic acid amplification reaction container including reaction liquid in which nucleic acid is eluted and oil phase-separated from the reaction liquid, (B) a control section for rotating the rotating body and moving the reaction liquid back and forth between a first region and a second region, and (C) a fluorescence measuring device for performing fluorescence measurement of the reaction liquid in a position along a rotation track of the nucleic acid amplification reaction container at the time when the rotating body rotates.

7 Claims, 23 Drawing Sheets

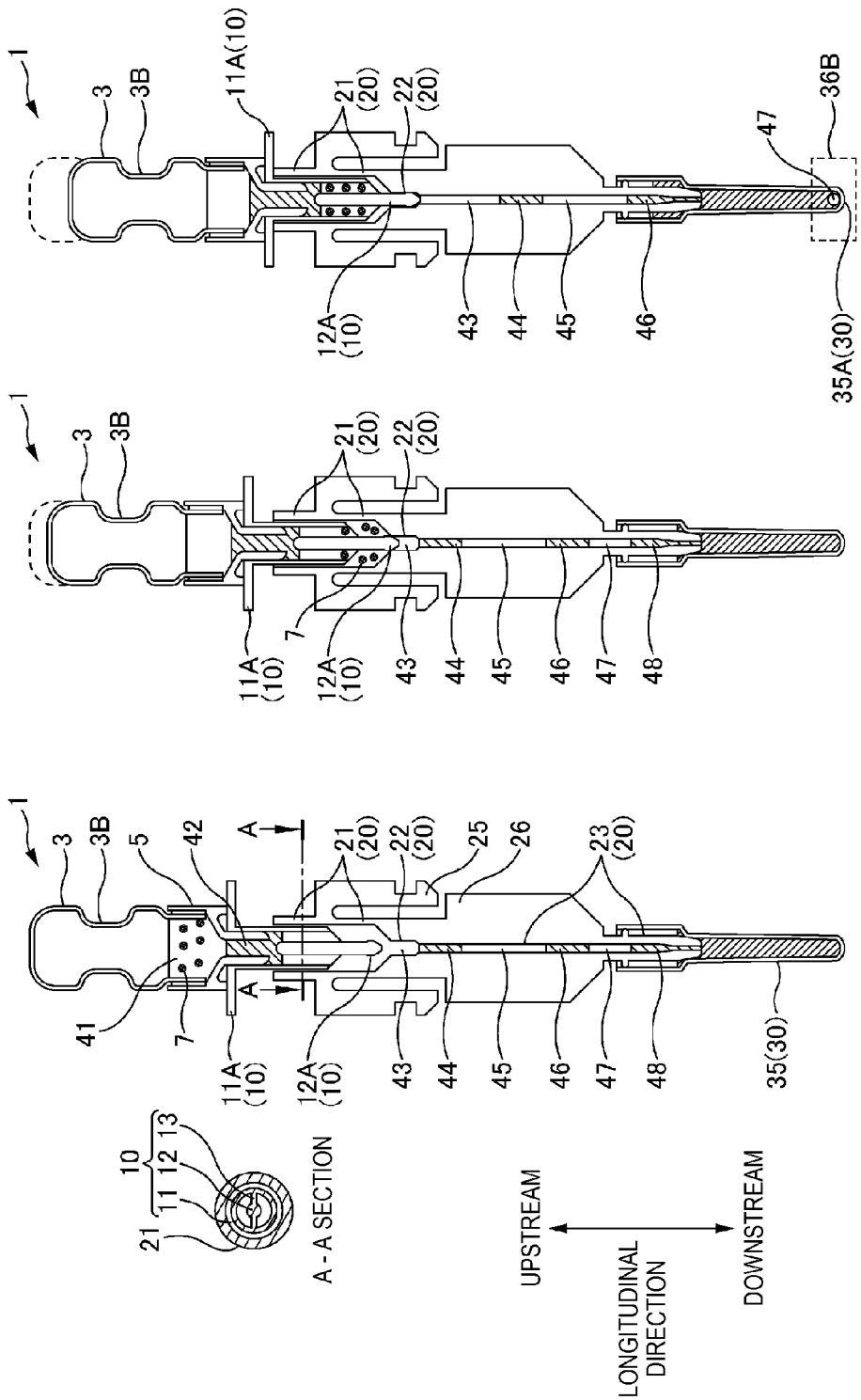

| POSITION OF A MAGNET | PRESENCE OR ABSENCE OF SWING |
|---|---|
| FIRST OIL PLUG | ABSENT |
| INTERFACE BETWEEN OIL AND CLEANING LIQUID | ABSENT |
| CLEANING LIQUID PLUG | PRESENT |
| INTERFACE BETWEEN CLEANING LIQUID AND OIL | ABSENT |
| SECOND OIL PLUG | ABSENT |
| INTERFACE BETWEEN OIL AND REACTION LIQUID | ABSENT |
| REACTION LIQUID PLUG | PRESENT |
| (DURING LIFTING OF THE MAGNET) | (ABSENT) |

FIG.13

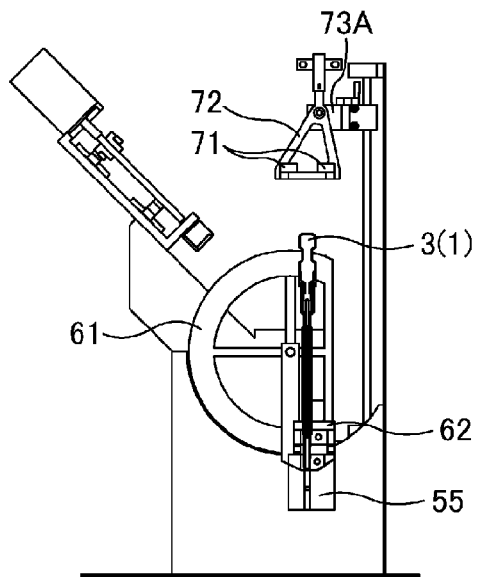 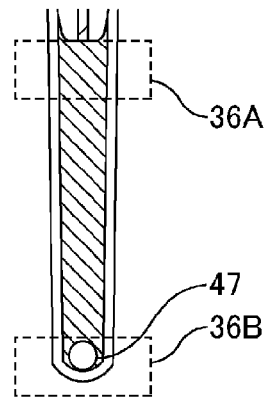
FIG.15A  FIG.15B
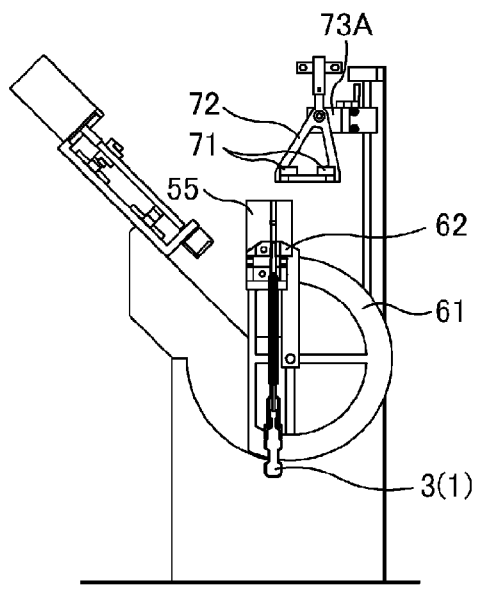 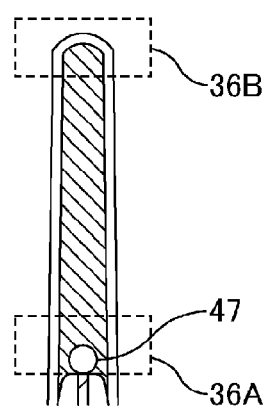
FIG.15C  FIG.15D

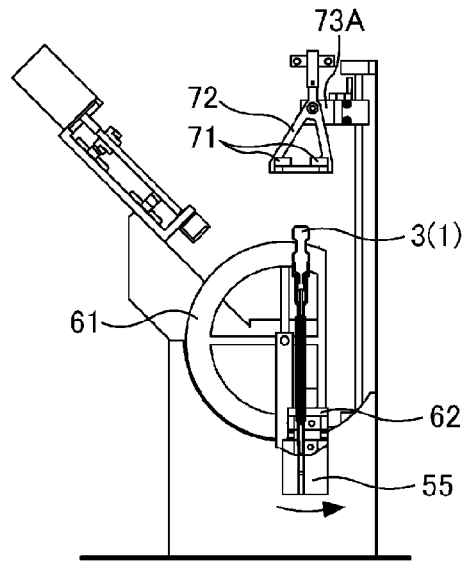 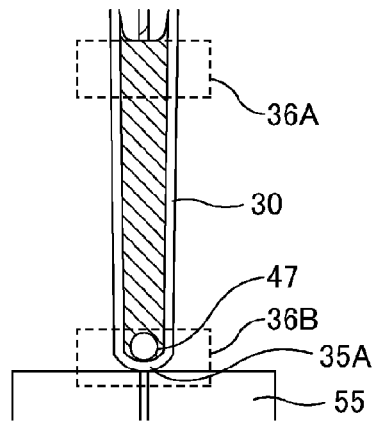
FIG.16A  FIG.16B
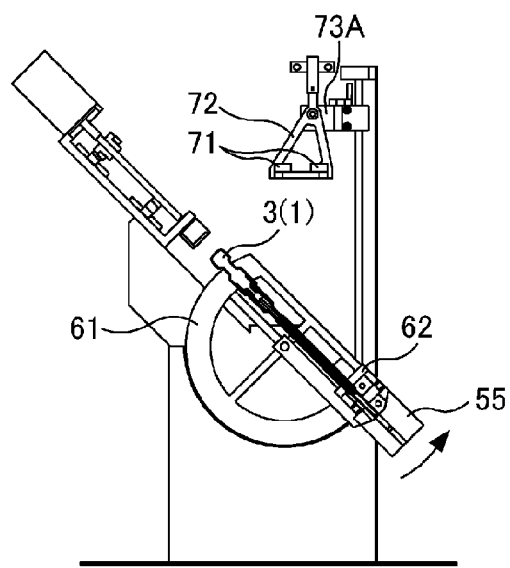 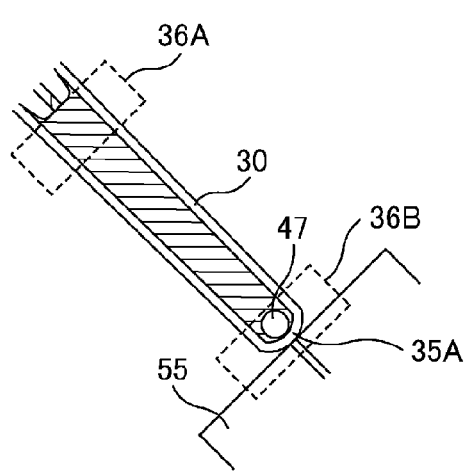
FIG.16C  FIG.16D

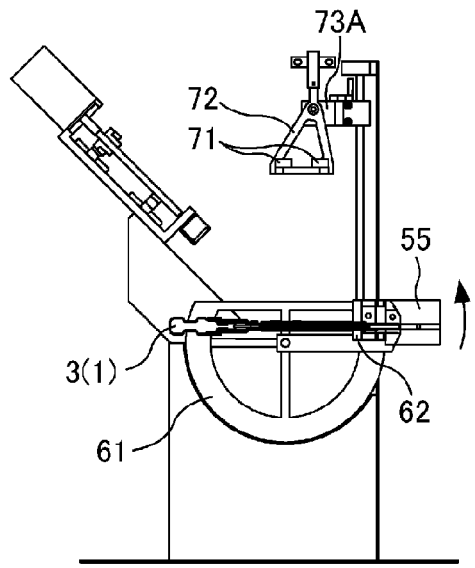
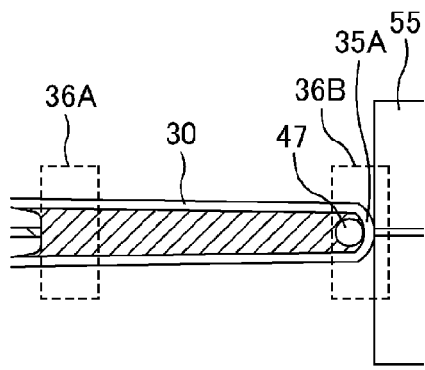
FIG.17A  FIG.17B
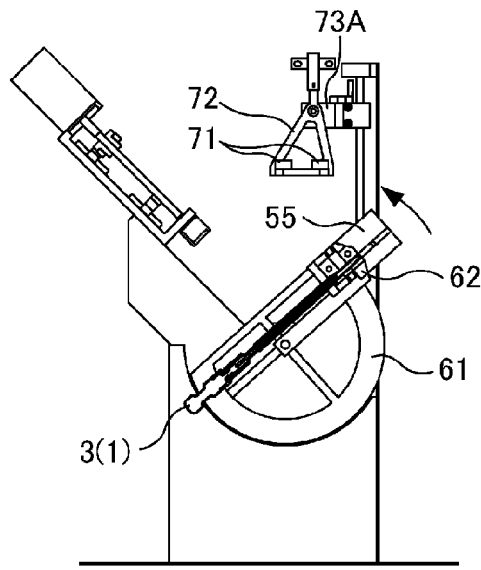
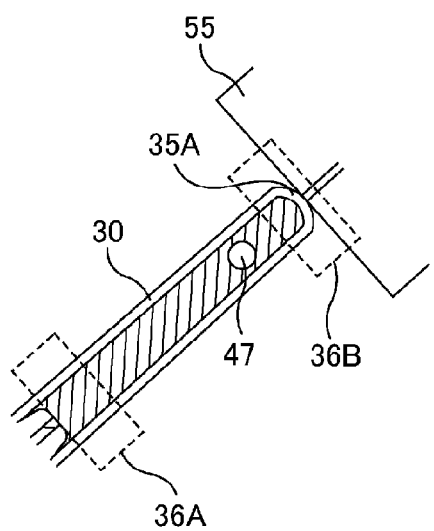
FIG.17C  FIG.17D

NUCLEIC ACID AMPLIFICATION REACTION APPARATUS AND NUCLEIC ACID AMPLIFYING METHOD

BACKGROUND

1. Technical Field

The present invention relates to a nucleic acid amplification reaction apparatus and a nucleic acid amplifying method.

2. Related Art

JP-A-2009-136250 (Patent Literature 1) and JP-A-2012-115208 (Patent Literature 2) disclose an apparatus that rotates a biochip filled with reaction liquid and oil phase-separated from the reaction liquid and having specific gravity smaller than the specific gravity of the reaction liquid to move the reaction liquid on the inside of the biochip and apply a heat cycle to the reaction liquid. However, in Patent Literatures 1 and 2, when real-time PCR is performed, a fluorescence measurement apparatus for performing fluorescence measurement of the reaction liquid is fixed in a specific position of a nucleic acid amplification reaction apparatus.

SUMMARY

An advantage of some aspects of the invention is to provide a nucleic acid amplification reaction apparatus and a nucleic acid amplifying method with high processing speed.

An aspect of the invention is directed to a nucleic acid amplification reaction apparatus including: (A) a rotating body mountable with a nucleic acid amplification reaction container including reaction liquid in which nucleic acid is eluted and oil phase-separated from the reaction liquid; (B) a control section for rotating the rotating body and moving the reaction liquid back and forth between a first region and a second region of the nucleic acid amplification reaction container; and (C) a fluorescence measuring device for performing fluorescence measurement of the reaction liquid in a position along a rotation track of the nucleic acid amplification reaction container at the time when the rotating body rotates.

Other characteristics of the invention are made apparent by the descriptions of this specification and accompanying drawings.

BRIEF DESCRIPTION OF THE DRAWINGS

The invention will be described with reference to the accompanying drawings, wherein like numbers reference like elements.

FIGS. 2A to 2C are operation explanatory diagrams of the cartridge.

FIG. 13 is a table showing presence or absence of the swing of the magnets.

FIGS. 15A to 15D are explanatory diagrams of heat cycle treatment.

FIGS. 16A and 16B is a first explanatory diagram of fluorescence measurement during rotation of the rotating body.

FIGS. 16C and 16D is a second explanatory diagram of the fluorescence measurement during the rotation of the rotating body.

FIGS. 17A and 17B is a third explanatory diagram of the fluorescence measurement during the rotation of the rotating body.

FIGS. 17C and 17D is a fourth explanatory diagram of the fluorescence measurement during the rotation of the rotating body.

DESCRIPTION OF EXEMPLARY EMBODIMENTS

Figures 1A, 1B:
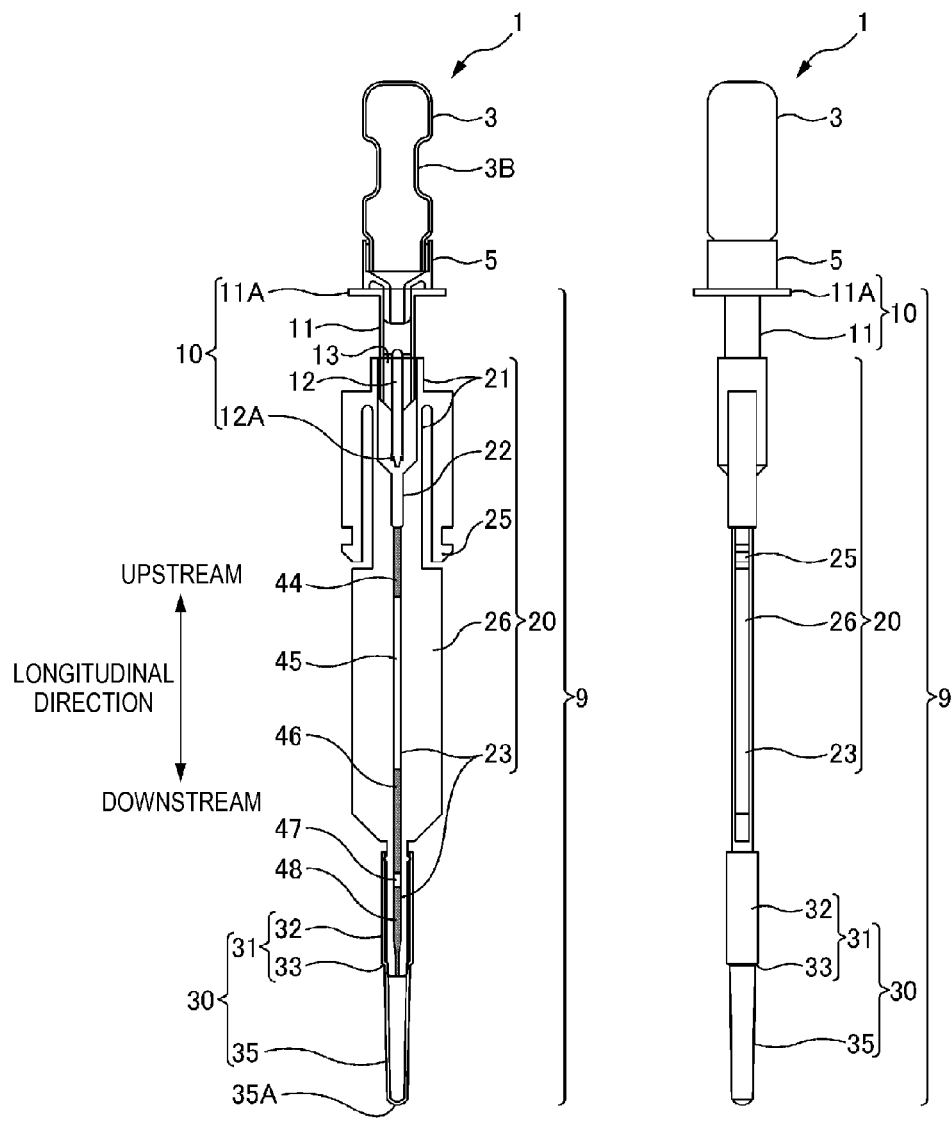
FIGS. 1A and 1B are explanatory diagrams of a cartridge.

At least matters explained below are made apparent by the descriptions of this specification and the accompanying drawings.

There is provided a nucleic acid amplification reaction apparatus including: a rotating body mountable with a nucleic acid amplification reaction container including reaction liquid in which nucleic acid is eluted and oil phase-separated from the reaction liquid; a control section for rotating the rotating body and moving the reaction liquid back and forth between a first region and a second region of the nucleic acid amplification reaction container; and a fluorescence measuring device for performing fluorescence measurement of the reaction liquid in a position along a rotation track of the nucleic acid amplification reaction container at the time when the rotating body rotates.

Consequently, it is possible to perform the fluorescence measurement of the reaction liquid in the position along the rotation track of the nucleic acid amplification reaction container while rotating the rotating body and moving the reaction liquid back and forth between the first region and the second region to supply a heat cycle. Therefore, it is possible to perform the fluorescence measurement while rotating the rotating body. Therefore, it is possible to reduce time in which the rotating body is stopped. Further, it is possible to reduce time per cycle of the heat cycle and provide the nucleic acid amplification reaction apparatus with high processing speed.

In the nucleic acid amplification reaction apparatus, it is preferable that the fluorescence measuring device rotates integrally with the rotating body.

Consequently, it is possible to rotate the fluorescence measuring device integrally with the rotating body. Therefore, it is possible to perform the fluorescence measurement of the reaction liquid in the position along the rotation track of the nucleic acid amplification reaction container while supplying the heat cycle to the reaction liquid.

The fluorescence measuring device may move according to the rotation of the rotating body along the rotation track of the nucleic acid amplification reaction container.

Consequently, it is possible to move the fluorescence measuring device itself along the rotation track of the nucleic acid amplification reaction container. Therefore, it is possible to perform the fluorescence measurement of the reaction liquid in the position along the rotation track of the nucleic acid amplification reaction container while supplying the heat cycle to the reaction liquid.

A detecting section of the fluorescence measuring device may move, according to the rotation of the rotating body, the position along the rotation track of the nucleic acid amplification reaction container.

Consequently, it is possible to move the detecting section of the fluorescence measuring device to the position along the rotation track. Therefore, it is possible to perform the fluorescence measurement of the reaction liquid on the basis of luminance detected via the detecting section.

The fluorescence measuring device may include a fluorescence measuring device main body section, the detecting section, and an optical fiber that connects the fluorescence measuring device main body section and the detecting section.

Consequently, it is possible to fix the fluorescence measuring device main body section itself in the nucleic acid amplification reaction apparatus, send the luminance of the reaction liquid detected by the detecting section to the fluorescence measuring device main body section via the optical fiber, and perform the fluorescence measurement of the reaction liquid.

It is preferable that the fluorescence measuring device performs the fluorescence measurement of the reaction liquid when the rotating body is rotating.

Consequently, it is possible to perform the fluorescence measurement of the reaction liquid by the fluorescence measuring device during the rotation of the rotating body. Therefore, it is possible to reduce a stop time of the rotating body. Further, it is possible to reduce time per cycle of the heat cycle.

A plurality of the fluorescence measuring devices may be arranged in positions along the rotation track of the nucleic acid amplification reaction container.

Consequently, the respective fluorescence measuring devices detect luminances in different wavelength regions. Therefore, it is possible to provide a nucleic acid amplification reaction apparatus of a multiplex type.

It is preferable that the nucleic acid amplification reaction apparatus includes a first heater that heats the first region and a second heater that heats the second region.

Consequently, it is possible to provide a first temperature in the first region. It is possible to provide a second temperature in the second region.

At least matters explained below are made apparent by the descriptions of this specification and the accompanying drawings.

There is provided a nucleic acid amplifying method including: rotating a nucleic acid amplification reaction container including reaction liquid in which nucleic acid is eluted and oil phase-separated from the reaction liquid and moving the reaction liquid back and forth between a first region and a second region of the nucleic acid amplification reaction container; and performing fluorescence measurement of the reaction liquid in a position along a rotation track of the nucleic acid amplification reaction container at the time when the rotating body is rotated.

Consequently, it is possible to perform the fluorescence measurement of the reaction liquid in the position along the rotation track of the nucleic acid amplification reaction container while rotating the rotating body and moving the reaction liquid back and forth between the first region and the second region to supply a heat cycle. Therefore, it is possible to perform the fluorescence measurement while rotating the rotating body. Therefore, it is possible to reduce time in which the rotating body is stopped. Further, it is possible to reduce time per cycle of the heat cycle and provide the nucleic acid amplification reaction apparatus with high processing speed.

First Embodiment

First, a cartridge mounted on a PCR apparatus 50 (a nucleic acid amplification reaction apparatus) is explained. Then, the configuration and the operation of the PCR apparatus 50 in this embodiment are explained.

Cartridge 1

FIGS. 1A and 1B are explanatory diagrams of a cartridge 1. FIGS. 2A to 2C are operation explanatory diagrams of the cartridge 1. FIG. 2A is an explanatory diagram of an initial state of the cartridge 1. FIG. 2B is a side view of the cartridge 1 in which a plunger 10 is pushed in a state shown in FIG. 2A and a seal 12A comes into contact with a lower syringe 22. FIG. 2C is an explanatory diagram of the cartridge 1 after the plunger 10 is pushed.

The cartridge 1 is a container for performing nucleic acid elusion treatment for eluding nucleic acid from magnetic beads 7 bound with the nucleic acid and is a container for applying heat cycle treatment for polymerase reaction to reaction liquid 47, which is a PCR solution.

The nucleic acid elution treatment is performed in a tank 3. The magnetic beads 7 are refined while passing through a tube 20. The material of the tube 20 is not particularly limited. However, the material of the tube 20 can be, for example, glass, resin such as plastics, and metal. In particular, it is more preferable to select transparent glass or resin as the material of the tube 20 because the inside of the tube 20 can be observed from the outside. It is preferable to select a substance or a nonmagnetic body, which transmits a magnetic force, as the material of the tube 20 because movement of magnetic particles is simplified by giving a magnetic force from the outside of the tube 20 when magnetic particles pass through the tube 20. It is preferable that the material of the tube 20 has heat resistance against heat at least equal to or higher than 100° C. because heaters (a heater for elution 65A and a high-temperature side heater 65B explained below) are arranged near the tube 20. The material of the tube 20 may be the same as the material of the tank 3.

The tube 20 includes a washing solution plug 45, a reaction liquid plug 47, and an oil plug. The magnetic beads 7 bound with the nucleic acid are attracted to an external magnet. Therefor, by moving the magnet on the outside along the tube 20, the magnetic beads 7 move in the tube 20 and reaches the reaction liquid plug 47 through the washing solution plug 45. The nucleic acid binding to the magnetic beads 7 is washed by the washing solution in the washing solution plug 45, and eluded in the reaction liquid plug 47. The "plug" means specific liquid occupying one section in the tube 20. For example, liquid retained in a columnar shape in a capillary 23 in FIGS. 2A to 2C is referred to as "plug". The oil is phase-separated from other solutions (are not mixed with the other solutions). Therefore, the plug formed by the oil has a function of preventing water soluble plugs on both sides of the plug from mixing with each other. In the plugs or among the plugs, it is preferable that air bubbles and other liquids are absent in the plugs or among the plugs. However, air bubbles and other liquids may be present as long as the magnetic beads 7 can pass through the plugs.

The type of the oil is not particularly limited. However, mineral oil, silicone oil (2CS silicone oil, etc.), vegetable oil, and the like can be used. By using oil having higher viscosity, it is possible to improve a "wiping effect" by the oil when a nucleic acid binding solid-phase carrier is moved on an interface with a plug on an upper side. Consequently, when the nucleic acid binding solid-phase carrier is moved from the plug on the upper side to the plug formed by the oil, it is possible to make it more difficult to carry a water soluble component adhering to the nucleic acid binding solid-phase carrier into the oil.

The heat cycle treatment is performed in a PCR container 30 of the cartridge 1. The PCR container 30 is filled with the oil. The reaction liquid 47 is phase-separated from the oil. Therefore, when the reaction liquid plug 47 is pushed out into the PCR container 30 from the tube 20, the reaction liquid plug 47 changes to a droplet shape. Since the reaction liquid plug 47 has specific gravity larger than the specific gravity of the oil, the droplet-like reaction liquid 47 precipitates. A high-temperature region 36A and a low-temperature region 36B are formed in the PCR container 30 by the external heater. When the entire cartridge 1 is repeatedly vertically reversed together with the heater, the droplet-like reaction liquid 47 alternately moves between the high-temperature region 36A and the low-temperature region 36B. Temperature treatment in two stages is applied to the reaction liquid 47, which is the PCR solution.

The material of the PCR container 30 is not particularly limited. However, the material of the PCR container 30 can be, for example, glass, resin such as plastics, and metal. It is preferable that the material of the PCR container 30 has heat resistance against heat at least equal to or higher than 100° C. because the high-temperature side heater 65B is present near the PCR container 30. It is preferable to select a transparent or semitransparent material as the material of the PCR container 30 because the fluorescence measurement (luminance measurement) can be easily performed. However, the entire region of the PCR container 30 does not need to be transparent or semitransparent. At least a part opposed to a fluorescence measuring device 55 (e.g., a bottom 35A of the PCR container 30) only has to be transparent or semitransparent. Note that the material of the PCR container 30 may be the same as the materials of the tank 3 and the plunger 10.

The cartridge 1 is configured by the tank 3 and a cartridge main body 9. In a kit for configuring the cartridge 1, an adapter 5 is prepared in advance together with the tank 3 and the cartridge main body 9. The tank 3 and the cartridge main body 9 are connected via the adapter 5, whereby the cartridge 1 is assembled. However, it is also possible to configure the tank 3 to be directly attached to the cartridge main body 9.

In the following explanation of the components of the cartridge 1, as shown in FIG. 2A, a direction along the long cartridge 1 is represented as "longitudinal direction", the tank 3 side is represented as "upstream side", and the PCR container 30 side is represented as "downstream side". The upstream side is sometimes simply represented as "upper" and the downstream side is sometimes represented as "lower".

(1) Tank

FIGS. 3A to 3D are explanatory diagrams of the tank 3.

Figure 3D:
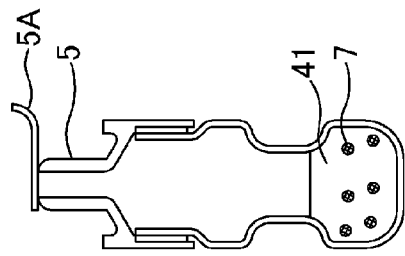
FIGS. 3A to 3D are explanatory diagrams of a tank.
Figure 3C:
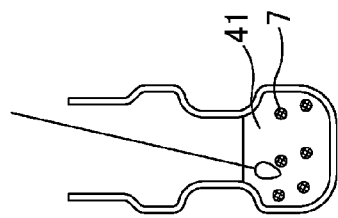
Figure 3B:
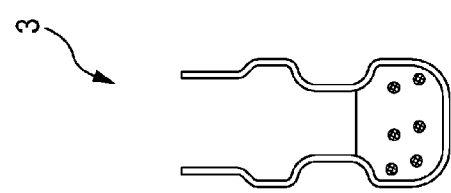
Figure 3A:
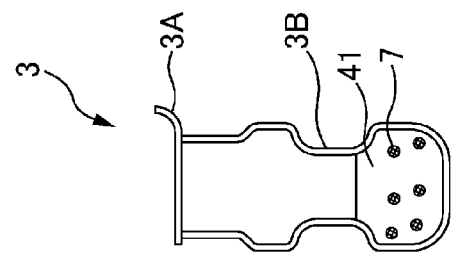

In the tank 3 prepared in advance in the kit, a solution 41 and the magnetic beads 7 are stored. A removable lid 3A is attached to an opening of the tank 3 (see FIG. 3A). As the solution 41, 5M guanidine thiocyanate, 2% Triton X-100, 50 mM Tris-HCl (pH 7.2) is used. An operator removes the lid 3A and opens the opening of the tank 3 (see FIG. 3B), immerses a cotton swab, to which a virus adheres, in the solution 41 in the tank 3, and collects the virus in the solution 41 (see FIG. 3C). When the liquid in the tank 3 is agitated, the tank 3 may be shaken in a state shown in FIG. 3C. However, since the solution 41 tends to overflow, as shown in FIG. 3D, it is preferable to attach the adapter 5 including a lid 5A to the opening of the tank 3 and then shake the tank 3. Consequently, the substances in the tank 3 are agitated, virus particles are dissolved by the solution 41, nucleic acid is isolated, and silica coated on the magnetic beads 7 adsorbs the nucleic acid. The magnetic beads 7 are equivalent to the nucleic acid binding solid-phase carrier. Thereafter, the operator removes the lid 5A of the adapter 5 attached to the opening of the tank 3 and attaches the tank 3 to the cartridge main body 9 via the adapter 5 (see FIG. 2A).

The tank 3 is formed of flexible resin. The tank 3 is expandable. When the plunger 10 slides and changes from the state shown in FIG. 2A to a state shown in FIG. 2B, the tank 3 expands, whereby the pressure of the liquid in the tube 20 is suppressed from excessively rising and the liquid in the tube 20 is suppressed from being pushed out to the downstream side. It is desirable to form a deformed section 3B in the tank 3 to allow the tank 3 to easily expand.

A sample for extracting and amplifying the nucleic acid is not limited to the virus and may be a cell. Derivation of the cell is not particularly limited and may be a microorganism or may be a tissue piece, blood, or the like of a higher organism.

The solution 41 is not particularly limited as long as the solution 41 contains a chaotropic substance. However, a surface active agent may be contained for the purpose of breaking a cell membrane or denaturing protein contained in the cell. In general, the surface active agent is not particularly limited as long as the surface active agent is used for nucleic acid extraction from a cell or the like. However, specifically, examples of the surface active agent include nonionic surface active agents including a triton-based surface active agent such as Triton-X and a Tween-based surface active agent such as Tween20 and anionic surface active agent such as N-sodium lauroylsarcosine (SDS). However, in particular, it is preferable to use the nonionic surface active agent in a range of 0.1 to 2%. Further, it is preferable to contain a reducing agent such as 2-mercaptoethanol or dithiothreitol in the solution. The solution may be a buffer solution. However, it is preferable that the solution is neutral liquid having pH 6 to pH 8. Taking these into account, specifically, it is preferable that the solution contains 3 to 7 M of guanidine salt, 0 to 5% of the nonionic surface active agent, 0 to 0.2 mM of EDTA, 0 to 0.2 M of the reducing agent, or the like.

The chaotropic substance is not particularly limited as long as the chaotropic substance has action of generating chaotropic ions (univalent anions having a large ion radius) in water solution and increasing water solubility of hydrophobic molecules and contributes to adsorption of nucleic acid to a solid-phase carrier. Specifically, examples of the chaotropic substance include guanidine thiocyanate, guanidine hydrochloride, sodium iodide, potassium iodide, and sodium perchlorate. However, among these, guanidine thiocyanate or guanidine hydrochloride having strong protein denaturation action is preferable. Concentrations of use of these chaotropic substances are different depending on the respective substances. For example, when guanidine thiocyanate is used, it is preferable to use guanidine thiocyanate in a range of 3 to 5.5 M. When guanidine hydrochloride is used, it is preferable to use guanidine hydrochloride at 5 M or higher.

An instrument for collecting a sample is not particularly limited. Instead of the cotton swab, a spatula, a bar, a scraper, or the like only has to be selected according to a use.

The internal volume of the tank 3 is not particularly limited. However, the internal volume of the tank 3 can be set to be, for example, equal to or larger than 0.1 mL and equal to or smaller than 100 mL. The material of the tank 3 is not particularly limited. However, the material of the tank 3 can be, for example, glass, resin such as plastics, and metal. In particular, it is more preferable to select transparent glass or resin as the material of the tank 3 because the inside of the tank 3 can be observed from the outside. The tank 3 and the tube 20 may be integrally molded or may be detachably attachable. When a flexible material such as rubber, elastomer, or polymer is used as the material of the tank 3, it is possible to pressurize the inside of the tank 3 by deforming the tank 3 in a state in which a lid is attached to the tank 3. Consequently, it is possible to push out, from the distal end side of the tube 20, content of the tube 20 from the inside to the outside of the tube 20.

(2) Cartridge Main Body

The cartridge main body 9 includes the plunger 10, the tube 20, and the PCR container 30.

(2-1) Plunger

The plunger 10 is explained below with reference to FIGS. 2A to 2C.

The plunger 10 is a movable plunger that pushes out liquid from the downstream side of the tube 20 functioning as a syringe. The plunger 10 has a function of pushing out a predetermined amount of liquid in the tube 20 from the end of the tube 20 to the PCR container 30. The plunger 10 also has a function of attaching the tank 3 via the adapter 5.

The plunger 10 includes a cylindrical section 11 and a bar-like section 12. The cylindrical section 11 is provided on the tank 3 side (the upstream side). The bar-like section 12 is provided on the tube 20 side (the downstream side). The bar-like section 12 is supported by tabular two ribs 13 on the inner wall on the downstream side of the cylindrical section 11. The downstream side of the bar-like section 12 projects to the downstream side from the cylindrical section 11.

The cylindrical section 11 is opened to the upstream side and the downstream side. The inner wall of the cylindrical section 11 functions as a passage of liquid. The adapter 5 is fit in the opening on the upstream side (the tank 3 side) of the cylindrical section 11. In the plunger 10 of the cartridge main body 9 prepared in the kit in advance, a detachable lid may be attached to the opening on the upstream side of the cylindrical section 11. The opening on the downstream side of the cylindrical section 11 is located on the inside of an upper syringe 21 of the tube 20. The magnetic beads 7 introduced from the opening on the upstream side of the cylindrical section 11 pass through the inside of the cylindrical section 11 and exit from the opening on the downstream side of the cylindrical section 11 through the front and the back of the ribs 13 to be introduced into the upper syringe 21 of the tube 20.

The downstream side of the cylindrical section 11 is fit in the inner wall of the upper syringe 21 of the tube 20. The cylindrical section 11 can slide in the longitudinal direction with respect to the upper syringe 21 while being inscribed in the upper syringe 21 of the tube 20.

An attachment stand 11A for attaching the adapter 5 is formed around the opening on the upstream side of the cylindrical section 11. The attachment stand 11A is also a part pushed when the plunger 10 is pushed. The attachment stand 11A is pushed, whereby the plunger 10 slides with respect to the tube 20 and changes from the state shown in FIG. 2A to a state shown in FIG. 2C. When the plunger 10 moves to the downstream side, the attachment stand 11A comes into contact with the upper edge of the tube 20 (see FIG. 2C). That is, an interval between the attachment stand 11A of the plunger 10 and the upper edge of the tube 20 is a slide length of the plunger 10.

In an initial state, the bar-like section 12 is located on the inside of the upper syringe 21 of the tube 20 and separated from the lower syringe 22 (see FIG. 2A). When the plunger 10 slides with respect to the tube 20, the bar-like section 12 is inserted into the lower syringe 22 of the tube 20. The bar-like section 12 slides in the downstream direction with respect to the lower syringe 22 while being inscribed in the lower syringe 22 (see FIGS. 2B and 2C).

The shape of a cross section orthogonal to the longitudinal direction of the bar-like section 12 is a circular shape. However, the sectional shape of the bar-like section 12 can be circular, elliptical, and polygonal shapes and is not particularly limited as long as the bar-like section 12 can fit in the inner wall of the lower syringe 22 of the tube 20.

The seal 12A is formed at the end on the downstream side of the bar-like section 12. When the seal 12A is fit in the lower syringe 22, the liquid in the tube 20 on the downstream side is prevented from flowing back to the upper syringe 21. When the plunger 10 is pushed from the state shown in FIG. 2B to the state shown in FIG. 2C, the liquid in the tube 20 is pushed out from the downstream side by an amount equivalent to a volume of sliding of the seal 12A in the lower syringe 22 during the pushing of the plunger 10.

The volume of the sliding of the seal 12A in the lower syringe 22 (the amount of the liquid in the tube 20 pushed out from the downstream side) is larger than a total amount of the reaction liquid plug 47 and a third oil plug 48 in the tube 20. Consequently, the liquid in the tube 20 can be pushed out not to leave the reaction liquid 47 in the tube 20.

The material of the plunger 10 is not particularly limited. However, the material of the plunger 10 can be, for example, glass, resin such as plastics, and metal. The cylindrical section 11 and the bar-like section 12 of the plunger 10 may be integrally formed of the same material or may be formed of different materials. The plunger 10 is formed by separately molding the cylindrical section 11 and the bar-like section 12 with resin and joining the cylindrical section 11 and the bar-like section 12 via the ribs 13.

Oil 42 and first washing solution 43 are stored on the inside of the plunger 10 in advance. Oil 42 in the plunger 10 has specific gravity smaller than the specific gravity of the first washing solution 43. Therefore, when the cartridge main body 9 is erected with the attachment stand 11A of the plunger 10 directed upward to attach the tank 3 to the cartridge main body 9, as shown in FIG. 2A, the oil 42 is arranged between the liquid in the tank 3 and the first washing solution 43 of the cartridge main body 9. As the oil 42, 2CS silicone oil is used. As the first washing solution 43, 8M guanidine hydrochloride, 0.7% Triton X-100 is used.

The first washing solution 43 only has to be liquid phase-separated from both of the oil 42 and oil 44 when mixed with the oils. The first washing solution 43 is preferably water or a low-salt concentration water solution. When the first washing solution 43 is the low-salt concentration water solution, the first washing solution 43 is preferably a buffer solution. The salt concentration of the low-salt concentration water solution is preferably equal to or lower than 100 mM, more preferably equal to or lower than 50 mM, and most preferably equal to or lower than 10 mM. There is no particular lower limit of the low-salt concentration water solution. However, the lower limit of the low-salt concentration water solution is preferably equal to or higher than 0.1 mM, more preferably equal to or higher than 0.5 mM, and most preferably equal to or higher than 1 mM. The solution may contain a surface active agent such as Triton, Tween, or SDS and pH of the solution is not particularly limited. Salt for changing the first washing solution 43 to the buffer solution is not particularly limited. However, salts such as Tris, HEPES, PIPES, and phosphoric acid are preferably used. Further, the washing solution preferably contains alcohol by an amount not inhibiting adsorption of nucleic acid to a carrier, reverse transcription reaction, PCR reaction, and the like. In this case, alcohol concentration is not particularly limited. The alcohol concentration may be equal to or lower than 70%, equal to or lower than 60%, equal to or lower than 50%, equal to or lower than 40%, equal to or lower than 30%, equal to or lower than 20%, or equal to or lower than 10%. However, the alcohol concentration is preferably equal to or lower than 5% or equal to or lower than 2%, more preferably equal to or lower than 1% or equal to or lower than 0.5%, and most preferably equal to or lower than 0.2% or equal to or lower than 0.1%.

A chaotropic agent may be contained in the first washing solution 43. For example, when guanidine hydrochloride is contained in the first washing solution 43, it is possible to wash particles and the like while maintaining or intensifying adsorption of nucleic acid adsorbed in the particles and the like. Concentration in containing guanidine hydrochloride can be set to be, for example, equal to or higher than 3 mol/L and equal to or lower than 10 mol/L and preferably equal to or higher than 5 mol/L and equal to or lower than 8 mol/L. If the concentration of guanidine hydrochloride is within this range, it is possible to wash other impurities and the like while more stably adsorbing nucleic acid adsorbed by the particles and the like.

(2-2) Tube

The tube 20 is explained with reference to FIGS. 2A to 2C.

The tube 20 has a cylindrical shape that can allow liquid to circulate in the longitudinal direction. The tube 20 includes the upper syringe 21, the lower syringe 22, and the capillary 23. Inner diameters of the sections vary stepwise.

The upper syringe 21 has a cylindrical shape that can allow liquid to circulate in the longitudinal direction. The cylindrical section 11 of the plunger 10 is slidably inscribed in the inner wall of the upper syringe 21. The upper syringe 21 functions as a syringe for the cylindrical section 11 of the plunger 10.

The lower syringe 22 has a cylindrical shape that can allow liquid to circulate in the longitudinal direction. The seal 12A of the bar-like section 12 of the plunger 10 can slidably fit in the inner wall of the lower syringe 22. The lower syringe 22 functions as a syringe for the bar-like section 12 of the plunger 10.

The capillary 23 has a capillary shape that can allow liquid to circulate in the longitudinal direction. The inner diameter of the capillary 23 is size for allowing liquid to maintain the shape of a plug and is 1.0 mm. At the end of the capillary 23 (the end on the downstream side of the tube 20), the inner diameter is smaller and is 0.5 mm. The inner diameter of the end of the capillary 23 is set smaller than the diameter (1.5 to 2.0 mm) of droplet-like reaction liquid explained below. Consequently, when the reaction liquid plug 47 is pushed out from the end of the capillary 23, it is possible to prevent the droplet-like reaction liquid from adhering to the end of the capillary 23 or flowing back into the capillary 23.

The capillary 23 only has to have a hollow on the inside and have a cylindrical shape that can allow liquid to circulate in the longitudinal direction. The capillary 23 may be bent in the longitudinal direction. However, the capillary 23 is preferably linear. Both of the size and the shape of the hollow on the inside of the tube 20 are not particularly limited as long as the liquid can maintain the shape of a plug in the tube 20. The size of the hollow in the tube 20 and the shape of a cross section of the tube 20 perpendicular to the longitudinal direction may change along the longitudinal direction of the tube 20.

The shape of a cross section perpendicular to longitudinal direction of the external shape of the tube 20 is not limited either. Further, the thickness (a dimension from the side surface of the hollow on the inside to the surface on the outside) of the tube 20 is not particularly limited either. When the tube 20 is cylindrical, the inner diameter (the diameter of a circle in a cross section perpendicular to the longitudinal direction of the hollow on the inside) can be set to be, for example, equal to or larger than 0.5 mm and equal to or smaller than 2 mm. When the inner diameter of the tube 20 is within this range, a plug of the liquid is easily formed in wide ranges of the material of the tube 20 and the type of the liquid. The distal end of the tube 20 is preferably narrowed in a taper shape and can be set to be equal to or larger than 0.2 mm and equal to or smaller than 1 mm. By setting the inner diameter of the end of the capillary 23 (the opening diameter of the capillary 23) small, it is possible to prevent a situation in which the reaction liquid 47 changed to droplets in the PCR container 30 adheres to the opening of the capillary 23 and does not separate from the opening. However, when the inner diameter of the end of the capillary 23 is set too small, the reaction liquid 47 in a form of a large number of small droplets is formed. When portions other than the end of the capillary 23 are reduced in diameter like the end of the capillary 23, the cartridge 1 undesirably increases in length because of necessity to secure the volumes of plugs.

The capillary 23 includes a first oil plug 44, the washing solution plug 45, a second oil plug 46, the reaction liquid plug 47, and the third oil plug 48 on the inside in order from the upstream side. That is, the oil plugs are arranged on both sides of the water-soluble plug (the washing solution plug 45 or the reaction liquid plug 47).

The upper syringe 21 and the lower syringe 22 further on the upstream side than the first oil plug 44, the oil 42 and the washing solution 43 are stored in advance (see FIG. 2A). The inner diameters of the upper syringe 21 and the lower syringe 22 are larger than the inner diameter of the capillary 23. In the upper syringe 21 and the lower syringe 22, the liquid (the oil 42 and the washing solution 43) cannot be maintained in a columnar shape like a plug. However, since the first oil plug 44 is retained in the shape of the plug by the capillary 23, the oil forming the first oil plug 44 is suppressed from moving to the upstream side.

The washing solution plug 45 may be formed by a 5 mM Tris hydrochloric acid buffer solution, which is the second washing solution. However, the second washing solution may be basically the same as the first washing solution. The second washing solution may be the same as or may be different from the first washing solution. However, the second washing solution is preferably a solution not practically including a chaotropic substance. This is for the purpose of eliminating the chaotropic substance carried into a solution following the solution. As explained above, the washing solution preferably contains alcohol by an amount not inhibiting adsorption of nucleic acid to a carrier, reverse transcription reaction, PCR reaction, and the like. In this case, alcohol concentration is not particularly limited. The alcohol concentration may be equal to or lower than 70%, equal to or lower than 60%, equal to or lower than 50%, equal to or lower than 40%, equal to or lower than 30%, equal to or lower than 20%, or equal to or lower than 10%. However, the alcohol concentration is preferably equal to or lower than 5% or equal to or lower than 2%, more preferably equal to or lower than 1% or equal to or lower than 0.5%, and most preferably equal to or lower than 0.2% or equal to or lower than 0.1%.

The washing solution plug 45 may be formed by a plurality of plugs divided by plugs of oil. When the washing solution plug 45 is formed by the plurality of plugs, liquids of the plugs may be the same or may be different. If at least one plug of washing solution is present among the plugs, the liquids of the other plugs are not particularly limited. However, all the plugs are preferably washing solutions. The number of divisions of the washing solution plug 45 can be set as appropriate taking into account, for example, the length of the tube 20, a washing target, and the like.

The reaction liquid plug 47 is formed of, for example, the following reaction liquids.

| | |
|---|---|
| 0.2 u/µL | AMV reverse transcription enzyme (Nippon Gene) |
| 0.125 u/µL | Gene Taq NT PCR enzyme (Nippon Gene) |
| 0.5 mM | dNTP |
| 1.0 µM | Primer (forward) |
| 1.0 µM | Primer (reverse) |
| 0.5 µM | Probe (Taq man) |
| 4.0 mg/mL | BSA |
| x1 | Buffer ($MgCl_2$ 7 mM: Tris pH 9.0 0.25 mM; KCl 50 mM) |

The reaction liquid 47 refers to liquid for eluting nucleic acid, which adheres to a nucleic acid binding solid-phase carrier, from the carrier to the liquid and performing reverse transcription reaction and polymerase reaction. Therefore, the reaction liquid 47 is prepared in advance such that the reaction liquid 47 after the elution of the nucleic acid changes to a buffer solution directly used for the revere transcription reaction and the polymerase reaction. Eluate for eluting the nucleic acid is included in the reaction liquid 47.

For the reverse transcription reaction, the reaction liquid 47 may contain a reverse transcription enzyme, dNTP, and a primer for the reverse transcription enzyme (oligonucleotide). Further, for the polymerase reaction, the reaction liquid may contain DNA polymerase and a primer for the DNA polymerase (oligonucleotide) and may contain a probe for real-time PCR such as a TaqMan probe, Molecular Beacon, or a cycling probe and a fluorescent dye for intercalator such as SYBR green. Further, the reaction liquid 47 preferably contains BSA (bovine serum albumin) or gelatin as a reaction inhibition prevention agent. A solvent is preferably water and more preferably an organic solvent such as ethanol or isopropyl alcohol and a solvent not practically containing a chaotropic substance. The reaction liquid 47 preferably contains salt to change to a buffer solution for the reverse transcription enzyme and/or a buffer solution for the DNA polymerase. The salt for changing the reaction liquid 47 to a buffer is not particularly limited as long as the salt does not inhibit enzyme reaction. However, salts such as Tris, HEPES, PIPES, and phosphoric acid are preferably used. The reverse transcription enzyme is not particularly limited. For example, reverse transcription enzymes derived from Avian Myeloblast Virus, Ras Associated Virus type 2, Mouse Molony Murine Leukemia virus, and Human Immunodeficiency Virus type 1 can be used. However, a heat resistant enzyme is preferable. The DNA polymerase is not particularly limited either. However, a heat resistant enzyme and an enzyme for PCR are preferable. For example, there are an extremely large number of commercially available products such as Taq polymerase, Tfi polymerase, Tth polymerase, and improvements of these polymerases. However, the DNA polymerase that can perform hot start is preferable.

The primer for the DNA polymerase can easily determine an appropriate array for DNA to be detected. Usually, in order to amplify one kind of DNA, the primer for the DNA polymerase only has to include a primer pair of a primer on a 5' side and a primer on a 3' side. In order to amplify a plurality of kinds of DNA, by including a plurality of kinds of primary pairs marked by different fluorescent dyes in the primer for the DNA polymerase, it is also possible to cope with a multiplex PCR. In that case, a plurality of the TaqMan probes only have to be included as appropriate.

The concentrations of dNTP and salt contained in the reaction liquid 47 only have to be set to concentrations suitable for enzyme in use. However, usually, the concentration of the dNTP only has to be set to 10 to 1000 µM and preferably 100 to 500 µM, the concentration of $Mg^{2+}$ only has to be set to 1 to 100 mM and preferably 5 to 10 mM, and the concentration of $Cl^-$ only has to be set to 1 to 2000 mM and preferably 200 to 700 mM. Total ion concentration is not particularly limited. However, the total ion concentration may be concentration higher than 50 mM. Concentration higher than 100 mM is preferable, concentration higher than 120 mM is more preferable, concentration higher than 150 mM is still more preferable, and concentration higher than 200 mM is yet still more preferable. An upper limit of the total ion concentration is preferably equal to or lower than 500 mM, more preferably equal to or lower than 300 mM, and still more preferably equal to or lower than 200 mM. Each of the oligonucleotides for the primer is used by 0.1 to 10 µM and preferably 0.1 to 1 µM. When the concentration of the BSA or the gelatin is equal to or lower than 1 mg/mL, a reaction inhibition prevention effect is little. When the concentration of the BSA or the gelatin is equal to or higher than 10 mg/mL, it is likely that the reverse transcription reaction and an enzyme reaction after the reverse transcription reaction are inhibited. Therefore, the concentration of the BSA or the gelatin is preferably 1 to 10 mg/mL. When the gelatin is used, examples of a derivation of the gelatin include cowhide, pig hide, and cow bone. However, the derivation is not particularly limited. When the gelatin is less easily dissolved, the gelatin may be heated and dissolved.

The volume of the reaction liquid plug 47 is not particularly limited and can be set as appropriate using, for example, an amount of particles or the like adsorbing nucleic acid as an index. For example, when the volume of the particles or the like is 0.5 µL, it is sufficient that the volume of the reaction liquid plug 47 is equal to or larger than 0.5 µL. The volume of the particles or the like is preferably set to be equal to or larger than 0.8 µL and equal to or smaller than 5 µL and more preferably equal to or larger than 1 µL and equal to or smaller than 3 µL. If the volume of the reaction liquid plug 47 is within these ranges, for example, even if the volume of the nucleic acid binding sold-phase carrier is set to 0.5 µL, it is possible to sufficiently elute nucleic acid from the carrier.

A downstream section of the capillary 23 is inserted into the PCR container 30. Consequently, it is possible to introduce the reaction liquid 47 into the PCR container 30 by pushing out the reaction liquid plug 47 in the tube 20 from the tube 20.

An annular convex section of the outer wall of the capillary 23 comes into contact with the inner wall of the PCR container 30, whereby an upper seal section is formed. The outer wall of the capillary 23 further on the downstream side than the upper seal section comes into contact with the inner wall of the PCR container 30, whereby a lower seal section is formed. The upper seal section and the lower seal section are explained below.

Figure 4:
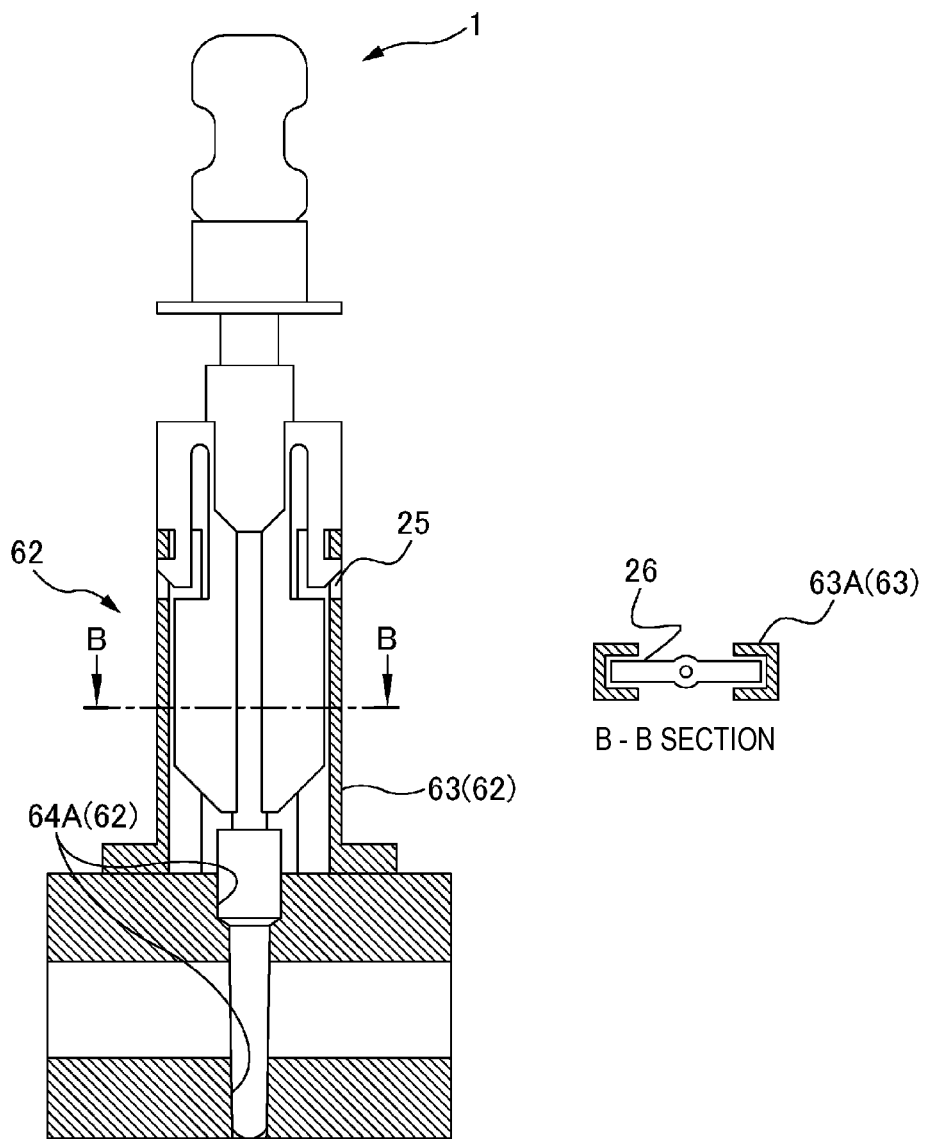
FIG. 4 is an explanatory diagram of fixing claws, a guide plate, and a mounting section.

The tube 20 further includes fixing claws 25 and a guide plate 26. FIG. 4 is an explanatory diagram of the fixing claws 25, the guide plate 26, and a mounting section 62.

The fixing claws 25 are members that fix the cartridge 1 to the mounting section 62. When the cartridge 1 is inserted into the mounting section 62 to be caught by the fixing claws 25, the cartridge 1 is fixed to a normal position with respect to the mounting section 62. In other words, when the cartridge 1 is present in an abnormal position with respect to the mounting section 62, the fixing claws 25 do not catch the mounting section 62.

The guide plate 26 is a member that guides the cartridge 1 when the cartridge 1 is mounted on the mounting section 62 of the PCR apparatus 50. A guide rail 63A is formed in the mounting section 62 of the PCR apparatus 50. The cartridge 1 is inserted into and fixed to the mounting section 62 while being guided by the guide plate 26 of the tube 20 along the guide rail 63A. The cartridge 1 has a long shape. However, since the cartridge 1 is inserted into the mounting section 62 while being guided by the guide plate 26, it is easy to fix the cartridge 1 in the normal position with respect to the mounting section 62.

The fixing claws 25 and the guide plate 26 are tabular members that project from the left and the right of the capillary 23. When the magnetic beads 7 in the tube 20 are moved by the magnet, the magnet is brought close to the magnetic beads 7 from a direction perpendicular to the tabular fixing claws 25 and the tabular guide plate 26. Consequently, it is possible to reduce the distance between the magnet and the magnetic beads 7 in the tube 20. However, the fixing claws 25 and the guide plate 26 may be formed in other shapes as long as the distance between the magnet and the magnetic beads 7 in the tube 20 can be reduced.

(2-3) PCR Container

Figures 5A, 5B:
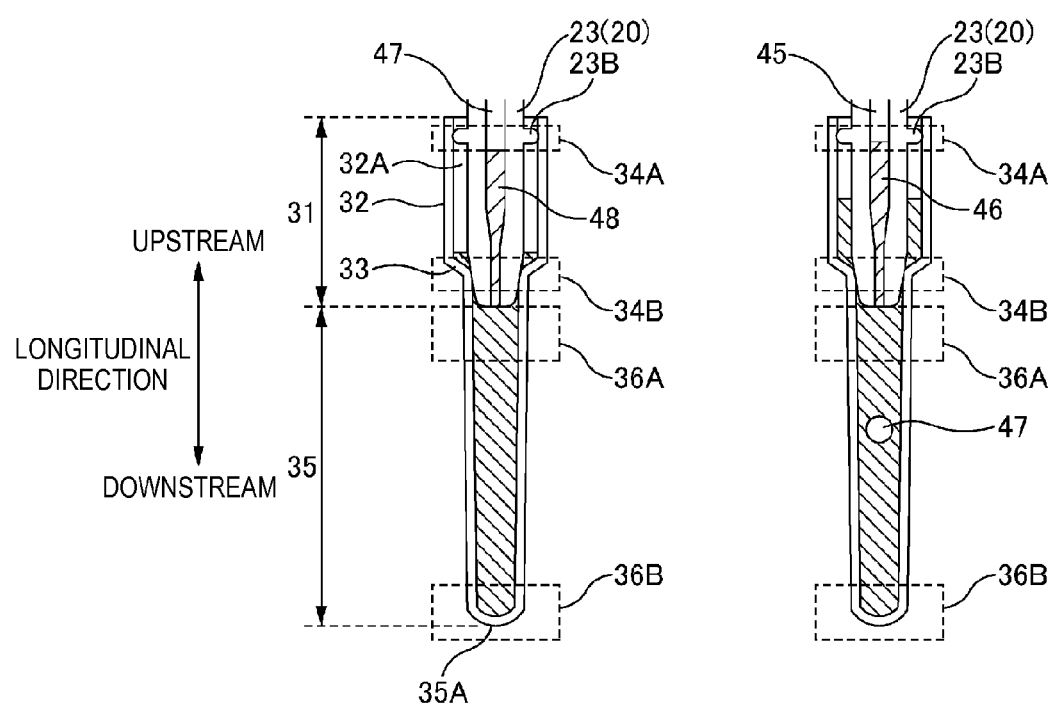
FIGS. 5A and 5B are explanatory diagrams of the periphery of a PCR container.

FIGS. 5A and 5B are explanatory diagrams of the periphery of the PCR container 30. FIG. 5A is an explanatory diagram of an initial state. FIG. 5B is an explanatory diagram of a state after the plunger 10 is pushed. The PCR container 30 is explained below with reference to FIGS. 2A to 2C as well.

The PCR container 30 is a container that receives liquid pushed out from the tube 20 and is a container that stores the reaction liquid 47 during the heat cycle treatment. The PCR container 30 is equivalent to the nucleic acid amplification reaction container.

The PCR container 30 includes a seal forming section 31 and a channel forming section 35. The seal forming section 31 is a section into which the tube 20 is inserted and is a part that suppresses oil overflowing from the channel forming section 35 from leaking to the outside. The channel forming section 35 is a section further on the downstream side than the seal forming section 31 and is a part that forms a channel through which the droplet-like reaction liquid 47 moves. The PCR container 30 is fixed to the tube 20 in two places, i.e., an upper seal section 34A and a lower seal section 34B of the seal forming section 31.

The seal forming section 31 includes an oil receiving section 32 and a step section 33.

The oil receiving section 32 is a cylindrical part and functions as a reservoir that receives the oil overflowing from the channel forming section 35. There is a gap between the inner wall of the oil receiving section 32 and the outer wall of the capillary 23 of the tube 20. The gap is an oil reception space 32A for receiving the oil overflowing from the channel forming section 35. The volume of the oil reception space 32A is larger than the volume of sliding of the seal 12A of the plunger 10 in the lower syringe 22 of the tube 20.

The inner wall on the upstream side of the oil receiving section 32 comes into contact with the annular convex section of the tube 20, whereby the upper seal section 34A is formed. The upper seal section 34A is a seal that suppresses the oil in the oil reception space 32A from leaking to the outside while allowing passage of the air. In the upper seal section 34A, a ventilation port is formed to a degree enough for preventing the oil from leaking with the surface tension of the oil. The ventilation port of the upper seal section 34A may be a gap between the convex section of the tube 20 and the inner wall of the oil receiving section 32 or may be a hole, a groove, or a cutout formed in the convex section of the tube 20. The upper seal section 34A may be formed by an oil absorbing material that absorbs the oil.

The step section 33 is a part having a step provided on the downstream side of the oil receiving section 32. The inner diameter of a downstream section of the step section 33 is smaller than the inner diameter of the oil receiving section 32. The inner wall of the step section 33 is in contact with the outer wall on the downstream side of the capillary 23 of the tube 20. The inner wall of the step section 33 and the outer wall of the tube 20 come into contact with each other, whereby the lower seal section 34B is formed. The lower seal section 34B is a seal that resists a flow of the oil in the channel forming section 35 while allowing the oil to flow to the oil reception space 32A. The pressure of the channel forming section 35 is higher than the outside pressure because of a pressure loss in the lower seal section 34B. Therefore, even if the liquid in the channel forming section 35 is heated during the heat cycle treatment, air bubbles are less easily formed in the liquid in the channel forming section 35.

The channel forming section 35 is a tubular part and is a container that forms a channel through which the droplet-like reaction liquid 47 moves. The oil is filled in the channel forming section 35. The upstream side of the channel forming section 35 is closed by the end of the tube 20. The end of the tube 20 is opened toward the channel forming section 35. The inner diameter of the channel forming section 35 is larger than the inner diameter of the capillary 23 of the tube 20 and is larger than the spherical shape of the liquid in the volume of the reaction liquid plug 47. The inner wall of the channel forming section 35 desirably has water repellency enough for preventing the water-soluble reaction liquid 47 from adhering to the inner wall.

The upstream side of the channel forming section 35 is heated to relatively high temperature (e.g., about 95° C.) by the external high-temperature side heater 65B and forms the high-temperature region 36A. The downstream side of the channel forming section 35 is heated to a relatively low temperature (e.g., about 60° C.) by an external low-temperature side heater 65C and forms the low-temperature region 36B. A bottom 35A (an end on the downstream side) of the PCR container is included in the low-temperature region 36B. Consequently, a temperature gradient is formed in the liquid in the channel forming section 35.

As shown in FIG. 5A, in the initial state, the oil is filled in the channel forming section 35 of the PCR container 30. The interface of the oil is located on a relatively downstream side of the oil reception space 32A. The volume further on the upstream side than the interface of the oil in the oil reception space 32A is larger than the volume of the sliding of the seal 12A of the plunger 10 in the lower syringe 22 of the tube 20.

As shown in FIG. 5B, when the plunger 10 is pushed, the liquid in the tube 20 is pushed out to the channel forming section 35. The oil is filled in the channel forming section 35 in advance. Since the liquid in the tube 20 is pushed out to the channel forming section 35, gas does not flow into the channel forming section 35.

When the plunger 10 is pushed, first, the third oil plug 48 of the tube 20 flows into the channel forming section 35. The oil equivalent to the third oil plug 48 flowing into the channel forming section 35 flows into the oil reception space 32A from the channel forming section 35. The oil interface of the oil reception space 32A rises. At this point, the pressure of the liquid in the channel forming section 35 rises because of a pressure loss of the lower seal section 34B. After the third oil plug 48 is pushed out from the tube 20, the reaction liquid plug 47 flows into the channel forming section 35 from the tube 20. Since the inner diameter of the channel forming section 35 is larger than the inner diameter of the capillary 23, the reaction liquid 47 having a plug shape (a columnar shape) in the tube 20 changes to a droplet shape in the oil in the channel forming section 35. The volume further on the upstream side than the interface of the oil in the initial state in the oil reception space 32A is larger than the volume of the sliding of the seal 12A of the plunger 10 in the lower syringe 22 of the tube 20. Therefore, the oil does not leak from the oil reception space 32A.

PCR Apparatus 50

Figure 6A:
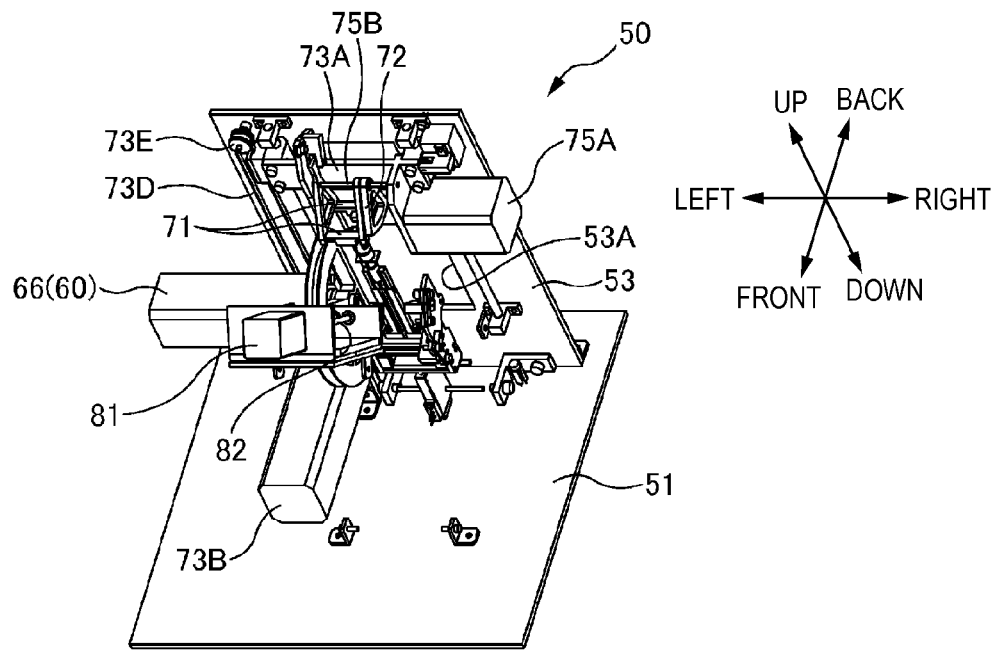
FIG. 6A is a perspective view of the internal configuration of a PCR apparatus.
Figure 6B:
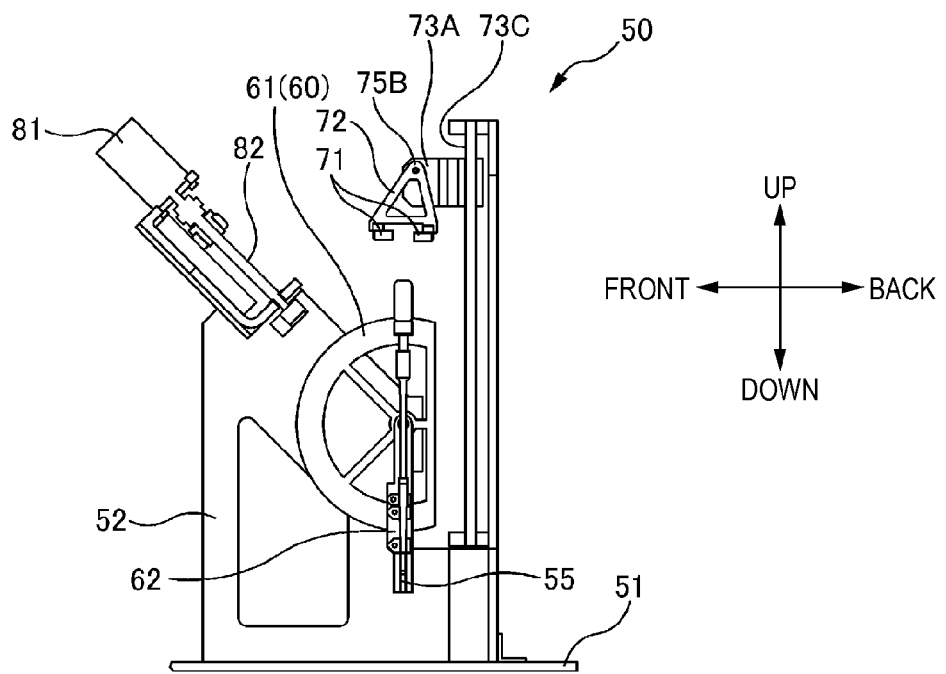
FIG. 6B is a side view of the main configuration of the PCR apparatus.
Figure 7:
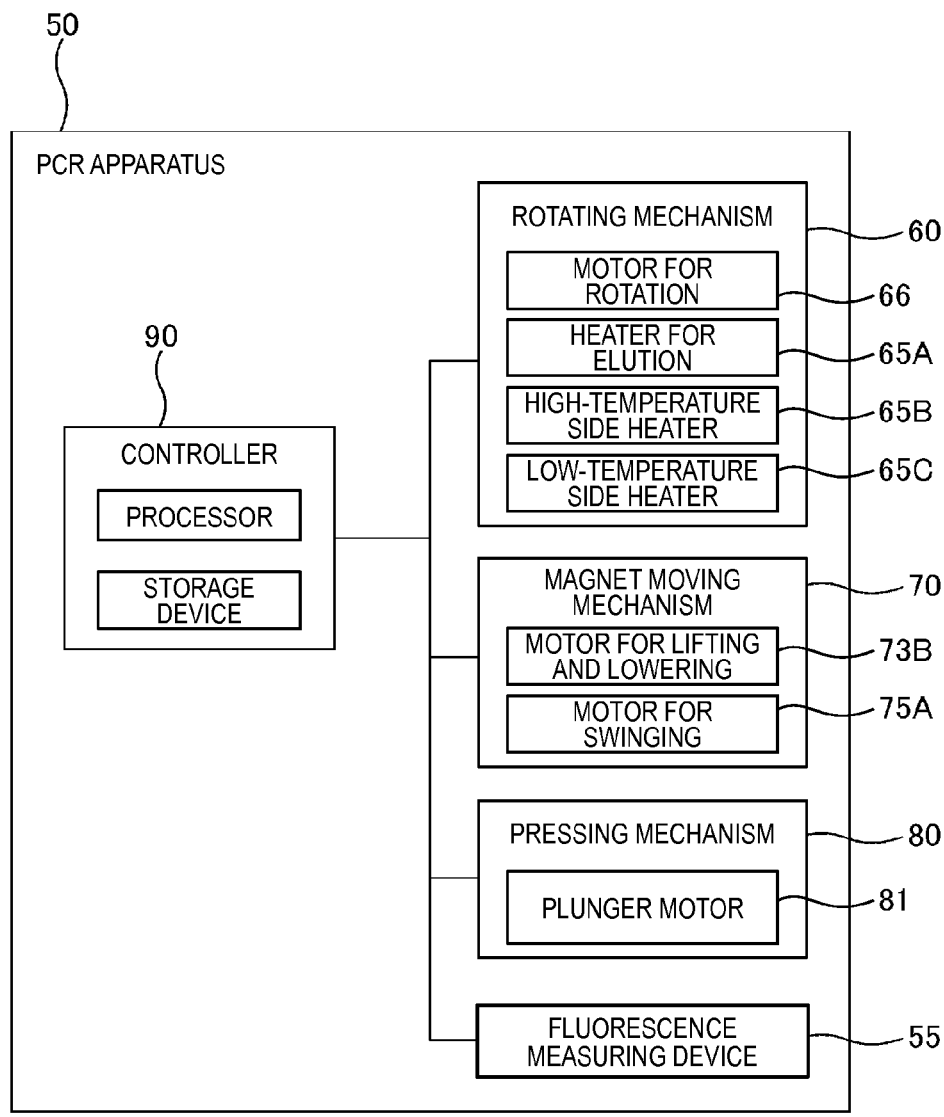
FIG. 7 is a block diagram of the PCR apparatus.

FIG. 6A is a perspective view of the internal configuration of the PCR apparatus 50. FIG. 6B is a side view of the main configuration of the PCR apparatus 50. FIG. 7 is a block diagram of the PCR apparatus 50. The PCR apparatus 50 performs the nucleic acid elution treatment and the heat cycle treatment using the cartridge 1.

In the following explanation of the PCR apparatus 50, up and down, the front and the back, the left and the right are defined as shown in the figures. That is, the vertical direction perpendicular to a horizontally-set base 51 of the PCR apparatus 50 is defined as "up-down direction". "UP" and "down" are defined according to the gravity direction. The axial direction of the rotation axis of the cartridge 1 is defined as "left-right direction" and a direction perpendicular to the up-down direction and the left-right direction is defined as "front-back direction". The side of a cartridge insertion port 53A viewed from the rotation axis of the cartridge 1 is defined as "rear" and the opposite side is defined as "front". The right side in the left-right direction viewed from the front side is defined as "right" and the left side is defined as "left".

The PCR apparatus 50 includes a rotating mechanism 60, a magnet moving mechanism 70, a pressing mechanism 80, a fluorescence measuring device 55, and a controller 90.

(1) Rotating Mechanism 60

The rotating mechanism 60 is a mechanism that rotates the cartridge 1 and heaters. The rotating mechanism 60 vertically reverses the cartridge 1 and the heaters, whereby the droplet-like reaction liquid 47 moves in the channel forming section 35 of the PCR container 30 and the heat cycle treatment is performed.

Figure 8A:
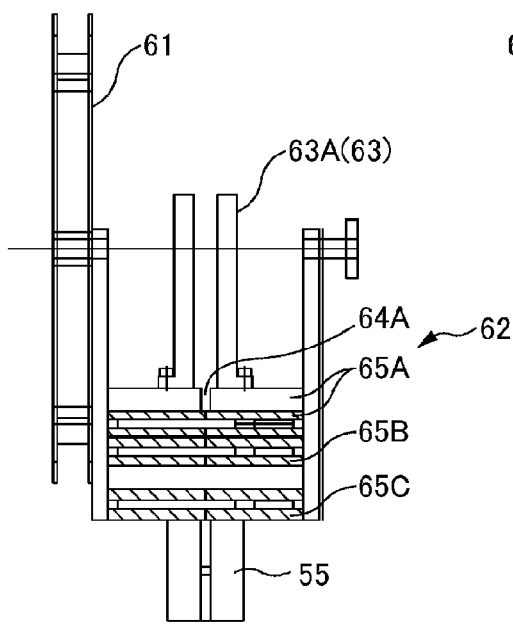
FIG. 8A is an explanatory diagram of a rotating body.
Figure 8B:
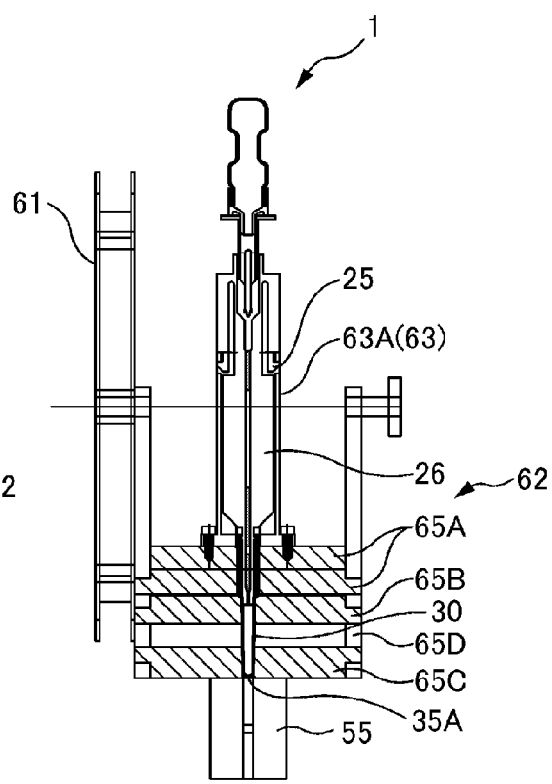
FIG. 8B is an explanatory diagram of a state in which the cartridge is mounted on the mounting section of the rotating body.

The rotating mechanism 60 includes a rotating body 61 and a motor for rotation 66. FIG. 8A is an explanatory diagram of the rotating body 61. FIG. 8B is an explanatory diagram of a state in which the cartridge 1 is mounted on the mounting section 62 of the rotating body 61.

The rotating body 61 is a member rotatable about the rotation axis. The rotation axis of the rotating body 61 is supported by a supporting stand 52 fixed to the base 51. In the rotating body 61, the mounting section 62 on which the cartridge 1 is mounted and the heaters (the heater for elution 65A, the high-temperature side heater 65B, and the low-temperature side heater 65C) are provided. When the rotating body 61 rotates, it is possible to vertically reverse the cartridge 1 while maintaining a positional relation between the cartridge 1 and the heaters. The motor for rotation 66 is a power source for rotating the rotating body 61. The motor for rotation 66 rotates the rotating body 61 to a predetermined position according to an instruction from the controller 90. A transmission mechanism such as a gear may be interposed between the motor for rotation 66 and the rotating body 61.

The rotation axis of the rotating body 61 is located closer to the tube 20 than the PCR container 30 of the cartridge 1. In other words, the height of the rotation shaft of the rotating body 61 is located at the height of the tube 20 of the cartridge 1 mounted on the mounting section 62. This is because, since the tube 20 is longer than the PCR container 30, if the center of the PCR container 30 is set as the rotation axis (if the height of the rotation axis of the rotating body 61 is located at the height of the PCR container 30), the rotating body 61 is increased in size.

The mounting section 62 is a part to which the cartridge 1 is attached. The mounting section 62 includes a fixing section 63 in which notches are formed. An insertion hole 64A formed in the heaters (the heater for elution 65A, the high-temperature side heater 65B, and the low-temperature side heater 65C) also functions as the mounting section 62. The fixing claws 25 of the cartridge 1 are caught by the notches of the fixing section 63 in a state in which the PCR container is inserted into the insertion hole 64A, whereby the cartridge 1 is attached to the rotating body 61 (see FIG. 4). A part of the heaters also functions as the mounting section 62. However, the mounting section 62 and the heaters may be separate. The mounting section 62 is indirectly fixed to the rotating body 61 via the heater for elution 65A. However, the mounting section 62 may be directly provided in the rotating body 61. The number of the cartridges 1 mountable on the mounting section 62 is not limited to one and may be plural.

The fixing section 63 of the mounting section 62 functions as a tube fixing section that fixes the tube 20 of the cartridge 1. The insertion hole 64A functions as a PCR-container fixing section that fixes the PCR container 30. Consequently, the long cartridge 1 including the tube 20 and the PCR container 30 is stably fixed to the mounting section 62.

In the fixing section 63, the guide rail 63A is formed along the up-down direction (see FIG. 4). The guide rail 63A guides the guide plate 26 of the cartridge 1 in an inserting direction while restraining the guide plate 26 in the front-back direction. Since the cartridge 1 is inserted into the mounting section 62 while the guide plate 26 is guided by the guide rail 63A, the PCR container 30 of the cartridge 1 is guided to the insertion hole 64A. The cartridge 1 is fixed in the normal position with respect to the mounting section 62.

The PCR apparatus 50 includes the heater for elution 65A and the high-temperature side heater 65B and the low-temperature side heater 65C functioning as heaters for PCR. The heaters include not-shown heat generation sources and heat blocks. The heat generation source is, for example, a cartridge heater and is inserted into the heat block. The heat block is, for example, metal such as aluminum having high thermal conductivity. The heat block suppresses heat unevenness and heats the liquid in the cartridge 1 with heat generated from the heat generation source. The heat block is desirably a non-magnetic body to prevent magnets 71 for moving the magnetic beads 7 from attracting the heat block.

The heater for elution 65A is a heater that heats the reaction liquid plug 47 of the cartridge 1. When the cartridge 1 is fixed in the normal position, the heater for elution 65A is opposed to the reaction liquid plug 47 of the tube 20. For example, the heater for elution 65A heats the reaction liquid plug 47 to about 50° C., whereby isolation of nucleic acid from the magnetic beads 7 is accelerated.

The high-temperature side heater 65B is a heater that heats the upstream side of the channel forming section 35 of the PCR container 30. When the cartridge 1 is fixed in the normal position, the high-temperature side heater 65B is opposed to the upstream side (the high-temperature region 36A) of the channel forming section 35 of the PCR container 30. For example, the high-temperature side heater 65B heats the liquid on the upstream side of the channel forming section 35 of the PCR container 30 to about 90 to 100° C.

The low-temperature side heater 65C is a heater that heats the bottom 35A of the channel forming section 35 of the PCR container 30. When the cartridge 1 is fixed in the normal position, the low-temperature side heater 65C is opposed to the downstream side (the low-temperature region 36B) of the channel forming section 35 of the PCR container 30. For example, the low-temperature side heater 65C heats the liquid in the low-temperature region 36B of the PCR container 30 to about 50 to 75° C.

A spacer 65D is arranged between the high-temperature side heater 65B and the low-temperature side heater 65C. The spacer 65D suppresses heat conduction between the high-temperature side heater 65B and the low-temperature side heater 65C. The spacer 65D is also used for accurately setting the distance between the high-temperature side heater 65B and the low-temperature side heater 65C. Consequently, a temperature gradient is formed in the liquid in the channel forming section 35 of the PCR container 30 by the high-temperature side heater 65B and the low-temperature side heater 65C.

In the heat blocks respectively configuring the heater for elution 65A, the high-temperature side heater 65B, and the low-temperature side heater 65C, through-holes forming the insertion hole 64A are respectively formed. The outer wall of the bottom 35A of the PCR container 30 is exposed from a lower side opening of the insertion hole 64A of the low-temperature side heater 65C. The fluorescence measuring device 55 measures the luminance of the reaction liquid 47 from the lower side opening of the insertion hole 64A.

Temperature control devices are respectively provided in the high-temperature side heater 65B and the low-temperature side heater 65C. The high-temperature side heater 65B and the low-temperature side heater 65C can be respectively set to temperatures suitable for polymerase reaction.

(2) Magnet Moving Mechanism 70

The magnet moving mechanism 70 is a mechanism that moves the magnets 71. The magnet moving mechanism 70 attracts the magnetic beads 7 in the cartridge 1 to the magnets 71 and moves the magnets 71 to thereby move the magnetic beads 7 in the cartridge 1. The magnet moving mechanism 70 includes a pair of magnets 71, a lifting and lowering mechanism 73, and a swinging mechanism 75.

The magnets 71 are members that attract the magnetic beads 7. A permanent magnet, an electromagnet, and the like can be used as the magnets 71. However, the permanent magnet not causing heat generation and the like is used. The pair of magnets 71 is retained by an arm 72 to be opposed to each other in the front-back direction and located in substantially the same positions in the up-down direction. The magnets 71 can be opposed to each other from the front side or the rear side of the cartridge 1 mounted on the mounting section 62. The pair of magnets 71 can hold the cartridge 1, which is mounted on the mounting section 62, from the front-back direction. The magnets 71 are opposed to each other in a direction (the front-back direction) orthogonal to the direction (the left-right direction) in which the fixing claws 25 or the guide plate 26 of the cartridge 1 are provided, whereby the distance between the magnetic beads 7 in the cartridge 1 and the magnets 71 can be reduced.

The lifting and lowering mechanism 73 is a mechanism that moves the magnets 71 in the up-down direction. Since the magnets 71 attract the magnetic beads 7, if the magnets 71 are moved in the up-down direction according to the movement of the magnetic beads 7, the magnetic beads 7 in the cartridge 1 can be attracted in the up-down direction.

The lifting and lowering mechanism 73 includes a carriage 73A that moves in the up-down direction and a motor for lifting and lowering 73B. The carriage 73A is a member movable in the up-down direction and is guided movably in the up-down direction by a carriage guide 73C provided on the sidewall 53 in which the cartridge insertion port 53A is present. The arm 72 that retains the pair of magnets 71 is attached to the carriage 73A. Therefore, when the carriage 73A moves in the up-down direction, the magnet 71 moves in the up-down direction. The motor for lifting and lowering 73B is a power source for moving the carriage 73A in the up-down direction. The motor for lifting and lowering 73B moves the carriage 73A to a predetermined position in the up-down direction according to an instruction from the controller 90. The motor for lifting and lowering 73B moves the carriage 73A in the up-down direction using a belt 73D and a pulley 73E. However, the motor for lifting and lowering 73B may move the carriage 73A in the up-down direction using other transmission mechanisms.

When the carriage 73A is present in a top position (a retracted position), the magnets 71 are located on the upper side than the cartridge 1. When the carriage 73A is present in the retracted position, the lifting and lowering mechanism 73 does not come into contact with the cartridge 1 even if the cartridge 1 rotates. The lifting and lowering mechanism 73 can lower the position of the carriage 73A to a position where the magnets 71 are opposed to a reaction plug. Consequently, the lifting and lowering mechanism 73 can move the magnets 71 to move the magnetic beads 7 in the tank 3 to the position of the reaction plug.

The swinging mechanism 75 is a mechanism that swings the pair of magnets 71 in the front-back direction. When the pair of magnets 71 is swung in the front-back direction, the intervals between the magnets 71 and the cartridge 1 alternately change. Since the magnetic beads 7 are attracted to the magnet 71 closer to the cartridge 1, by swinging the pair of magnets 71 in the front-back direction, the magnetic beads 7 in the cartridge 1 move in the front-back direction.

The swinging mechanism 75 includes a motor for swinging 75A and a gear. The motor for swinging 75A and the gear are provided in the carriage 73A and can move in the up and down direction together with the carriage 73A. The power of the motor for swinging 75A is transmitted to the arm 72 via the gear, whereby the arm 72 that retains the magnets 71 rotates about a swing rotation axis 75B with respect to the carriage 73A. In order to prevent the magnets 71 from coming into contact with the cartridge 1 to damage the cartridge 1, the swinging mechanism 75 swings the magnets 71 in a range in which the magnets 71 and the cartridge 1 do not come into contact with each other.

The swing rotation axis 75B is the rotation axis of arm 72. The swing rotation axis 75B is parallel to the left-right direction such that the magnets 71 can be swung in the front-back direction. When the swing rotation axis 75B is viewed from the right or the left, the swing rotation axis 75B is arranged to be shifted further to the front side or the rear side than the cartridge 1. Consequently, when the carriage 73A moves downward, contact of the cartridge 1 and the arm 72 can be avoided. If the magnets 71 can be swung in the front-back direction, the swing rotation axis 75B may be an axis parallel to the up-down direction.

(3) Pressing Mechanism 80

The pressing mechanism 80 is a mechanism that pushes the plunger 10 of the cartridge 1. The plunger 10 is pushed by the pressing mechanism 80, whereby the reaction liquid plug 47 and the oil plug in the cartridge 1 are pushed out to the PCR container 30. The droplet-like reaction liquid 47 is formed in the oil in the PCR container 30.

The pressing mechanism 80 includes a plunger motor 81 and a rod 82. The plunger motor 81 is a power source that moves the rod 82. The rod 82 is a member that pushes an attachment stand 11A of the plunger 10 of the cartridge 1. The attachment stand 11A is pushed rather than the tank 3 of the cartridge 1 because the tank 3 is formed of flexible resin to be capable of expanding. When the tank 3 is not deformed, the pressing mechanism 80 may push the tank 3 to thereby push the plunger 10.

A direction in which the rod 82 pushes the plunger 10 is not the up-down direction and tilts at 45 degrees with respect to the up-down direction. Consequently, when the plunger 10 is pushed by the pressing mechanism 80, the PCR apparatus 50 rotates the rotating body 61 45 degrees, adjusts the longitudinal direction of the cartridge 1 to the moving direction of the rod 82, and then moves the rod 82. Since the direction in which the rod 82 pushes the plunger 10 tilts at 45 degrees with respect to the up-down direction, it is easy to arrange the pressing mechanism 80 not to interfere with the lifting and lowering mechanism 73. Since the direction in which the rod 82 pushes the plunger 10 tilts at 45 degrees with respect to the up-down direction, the dimension in the up-down direction of the PCR apparatus 50 can be reduced.

(4) Fluorescence Measuring Device 55

The fluorescence measuring device 55 is a measuring device that measures the luminance of the reaction liquid 47 in the PCR container 30. The fluorescence measuring device 55 is fixed to the mounting section 62 to be located in a position opposed to the bottom 35A of the PCR container 30 of the cartridge 1. That is, the fluorescence measuring device 55 is fixed to be capable of rotating integrally with the rotating body 61. When the rotating body 61 rotates, the fluorescence measuring device 55 moves on a rotation track according to the rotation of the rotating body 61.

The fluorescence measuring device 55 measures the luminance of the reaction liquid 47 present in the bottom 35A of the PCR container 30 from the lower side opening of the insertion hole 64A of the low-temperature side heater 65C. The fluorescence measuring device 55 is desirably capable of detecting luminances in a plurality of wavelength regions to be adaptable to multiplex PCR.

(5) Controller 90

The controller 90 is a control section that performs control of the PCR apparatus 50. The controller 90 includes a processor such as a CPU and a storage device such as a ROM or a RAM. Various computer programs and data are stored in the storage device. The storage device provides a region in which the computer programs are expanded. The processor executes the computer programs stored in the storage device, whereby various kinds of processing are realized.

For example, the controller 90 controls the motor for rotation 66 to rotate the rotating body 61 to a predetermined rotating position. A not-shown rotating position sensor is provided in the rotating mechanism 60. The controller 90 drives and stops the motor for rotation 66 according to a detection result of the rotating position sensor.

The controller 90 controls the heaters (the heater for elution 65A, the high-temperature side heater 65B, and the low-temperature side heater 65C) and causes the heaters to generate heat. Not-shown temperature sensors are provided in the heat blocks configuring the heaters. The controller 90 controls ON and OFF of the cartridge heater according to detection results of the temperature sensors.

The controller 90 controls the motor for lifting and lowering 73B to move the magnets 71 in the up-down direction. A not-shown position sensor that detects the position of the carriage 73A is provided in the PCR apparatus 50. The controller 90 drives and stops the motor for lifting and lowering 73B according to a detection result of the position sensor.

The controller 90 controls the motor for swinging 75A to swing the magnets 71 in the front-back direction. In the PCR apparatus 50, a position sensor that detects the position of the arm 72, which retains the magnets 71, is provided. The controller 90 drives and stops the motor for swinging 75A according to a detection result of the position sensor.

The controller 90 controls the fluorescence measuring device 55 to measure the luminance of the reaction liquid 47 in the PCR container 30. When the fluorescence measuring device 55 is opposed to the bottom 35A of the PCR container 30 of the cartridge 1, the controller 90 causes the fluorescence measuring device 55 to perform measurement. A measurement result is stored in the storage device.

Explanation of Operation (1) Mounting Operation of the Cartridge 1

Figures 9A, 9B:
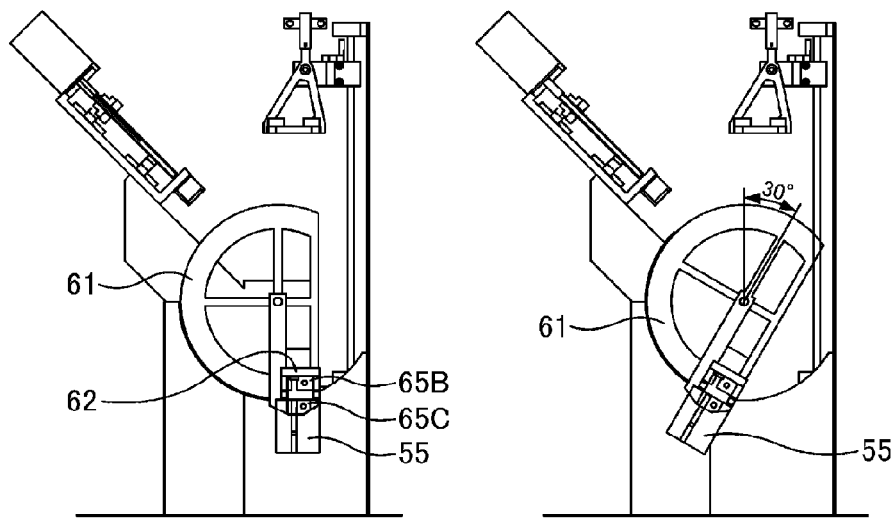
FIGS. 9A to 9D are explanatory diagrams of states of the PCR apparatus during the attachment of the cartridge.
Figures 9C, 9D:
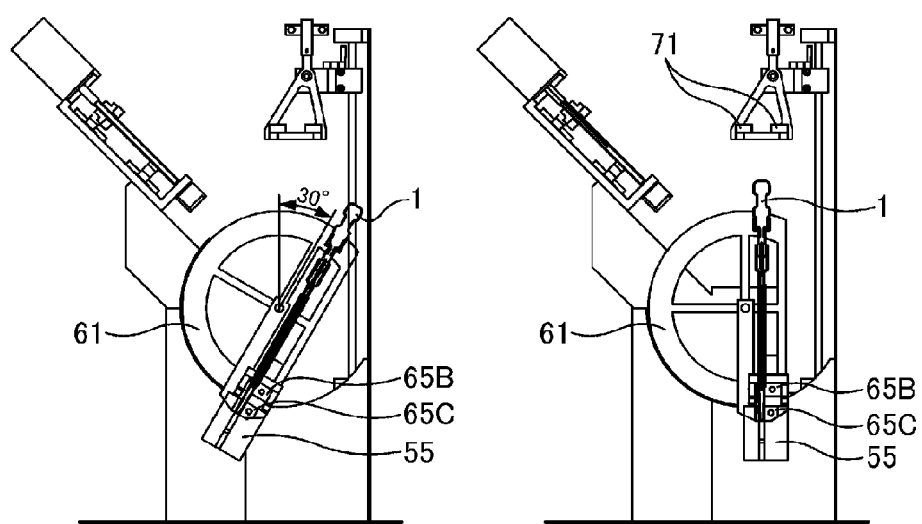

FIGS. 9A to 9D are explanatory diagrams of a state of the PCR apparatus 50 during mounting of the cartridge 1. FIG. 9A is an explanatory diagram of an initial state before the mounting of the cartridge 1. FIG. 9B is an explanatory diagram of a standby state. FIG. 9C is an explanatory diagram immediately after the mounting of the cartridge 1. FIG. 9D is an explanatory diagram of an initial state in a mounted state of the cartridge 1.

As shown in FIG. 9A, in the initial state before the mounting of the cartridge 1, a mounting direction of the mounting section 62 is the up-down direction. In the following explanation, a rotating position of the rotating body 61 in this state is set as a reference (0 degree) and the counterclockwise direction viewed from the right is set as a positive direction to show a rotating position of the rotating body 61.

As shown in FIG. 9B, the controller 90 drives the motor for rotation 66 to rotate the rotating body 61 to −30 degrees. In this state, the operator inserts the cartridge 1 into the mounting section 62 from the cartridge insertion port 53A. At this point, the cartridge 1 is inserted into the mounting section 62 while the guide plate 26 is guided by the guide rail 63A. Therefore, the PCR container 30 of the cartridge 1 is guided to the insertion hole 64A of the mounting section 62. The operator inserts the cartridge 1 until the fixing claws 25 of the cartridge 1 are caught by the notches of the fixing section 63. Consequently, the cartridge 1 is fixed in the normal position with respect to the mounting section 62. If the PCR container 30 is not inserted into the insertion hole 64A and the cartridge 1 is present in the abnormal position with respect to the mounting section 62, the fixing claws 25 of the cartridge 1 are not caught by the notches of the fixing section 63. Therefore, the operator can recognize that the cartridge 1 is present in the abnormal position.

As shown in FIG. 9C, when the cartridge 1 is fixed in the normal position with respect to the mounting section 62, the reaction liquid plug 47 of the tube 20 is opposed to the heater for elution 65A, the upstream side (the high-temperature region 36A) of the channel forming section 35 of the PCR container 30 is opposed to the high-temperature side heater 65B, and the downstream side (the low-temperature region 36B) of the channel forming section 35 of the PCR container 30 is opposed to the low-temperature side heater 65C. Since the mounting section 62 and the heaters are provided in the rotating body 61, even if the rotating body 61 rotates, the positional relation between the cartridge 1 and the heaters is maintained.

After the cartridge 1 is mounted on the mounting section 62, as shown in FIG. 9D, the controller 90 rotates the rotating body 61 30 degrees and returns the position of the rotating body 61 to the reference. The controller 90 may detect the mounting of the cartridge 1 on the mounting section 62 with a not-shown sensor or according to input operation from the operator.

(2) Nucleic Acid Elution Treatment

Up Down Movement of the Magnets 71

Figure 10:
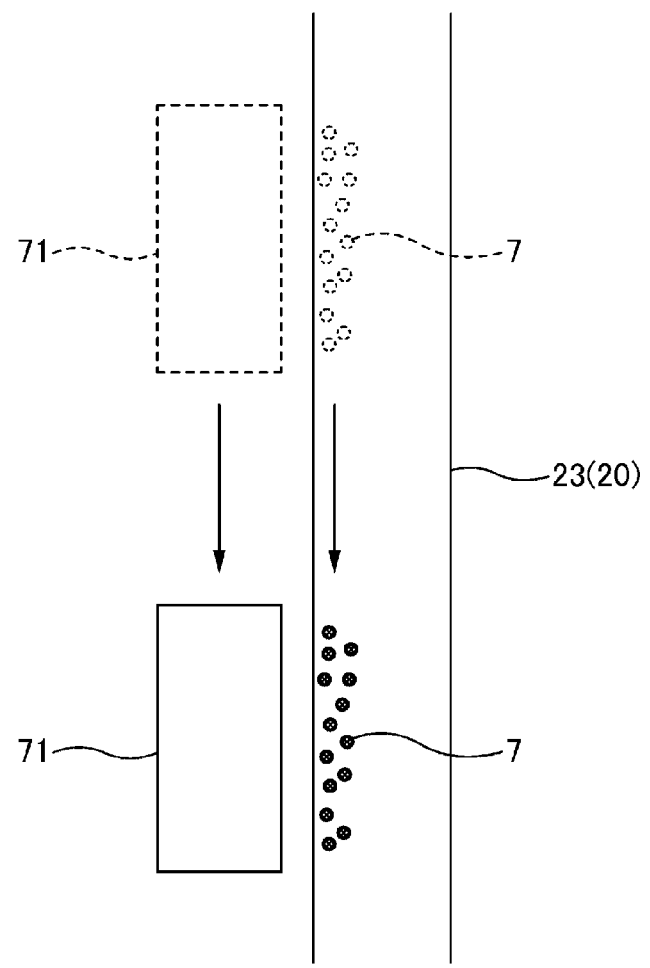
FIG. 10 is a conceptual diagram of the behavior of magnetic beads at the time when magnets are moved in a downward direction.

FIG. 10 is a conceptual diagram of the behavior of the magnetic beads 7 at the time when the magnets 71 are moved in the downward direction. The magnetic beads 7 in the cartridge 1 are attracted by the magnets 71. Therefore, when the magnets 71 move on the outside of the cartridge 1, the magnetic beads 7 in the cartridge 1 move together with the magnets 71.

Figures 11A, 11B:
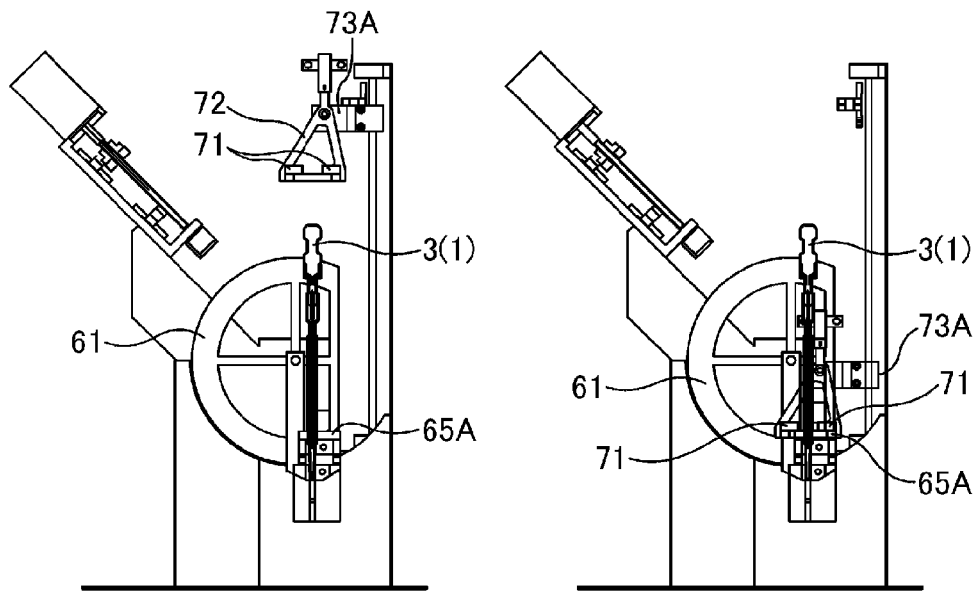
FIGS. 11A to 11C are explanatory diagrams of nucleic acid elution treatment.
Figure 11C:
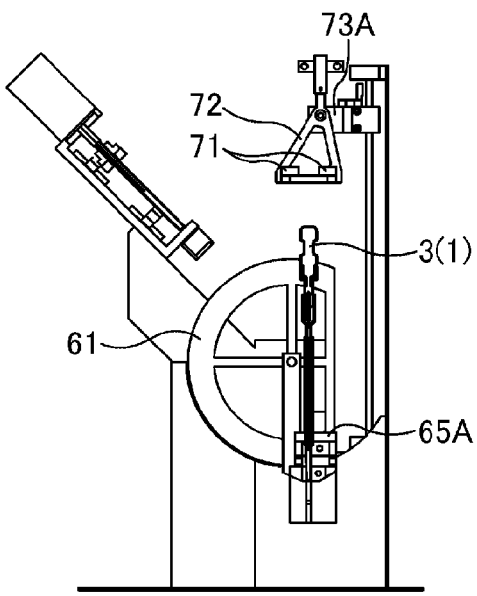

FIGS. 11A to 11C are explanatory diagrams of the nucleic acid elution treatment. FIG. 11A is an explanatory diagram of a state of the PCR apparatus 50 before the nucleic acid elution treatment. FIG. 11B is an explanatory diagram of a state of the PCR apparatus 50 at the time when the magnets 71 are moved to the reaction liquid plug 47. FIG. 11C is an explanatory diagram of a state of the PCR apparatus 50 at the time when the magnets 71 are lifted.

As shown in FIG. 11A, in the cartridge 1 in the initial state, the longitudinal direction is parallel to the vertical direction with the tank 3 set on the upper side. In this state, as shown in FIG. 2A, the cartridge 1 includes, in order from the top, the solution 41 (the tank 3) including the magnetic beads 7, the oil 42 (the plunger 10), the washing solution 43 (the upstream side of the tube 20), the first oil plug 44 (the capillary 23), the washing solution plug 45 (the capillary 23), the second oil plug 46 (the capillary 23), the reaction liquid plug 47 (the capillary 23), the third oil plug 48 (the capillary 23), and the oil (the PCR container 30).

As shown in FIG. 11A, in the initial state, the carriage 73A is present in the top position (the retracted position) and the magnets 71 are located on the upper side than the cartridge 1. In this state, the controller 90 drives the motor for lifting and lowering 73B, gradually moves the carriage 73A in the downward direction, and gradually moves the magnets 71 in the downward direction. Since the longitudinal direction of the cartridge 1 is parallel to the vertical direction, the magnets 71 move along the cartridge 1.

When the magnets 71 move in the downward direction, the magnets 71 are opposed to the tank 3. The magnetic beads 7 in the tank 3 are attracted to the magnets 71. The controller 90 moves the carriage 73A in the downward direction at speed for allowing the magnetic beads 7 to move together with the magnets 71.

When the magnets 71 move from a position opposed to the tank 3 (the height of the tank 3) to a position opposed to the plunger 10 (the height of the plunger 10), the magnetic beads 7 pass the opening on the upstream side of the cylindrical section 11 of the plunger 10 and pass the interface between the solution 41 in the tank 3 and the oil 42 on the upstream side of the cartridge main body 9. Consequently, the magnetic beads 7 bound with nucleic acid are introduced into the cartridge main body 9. When the magnetic beads 7 pass the interface with the oil 42, the solution 41 is wiped by the oil 42. Therefore, components of the solution 41 are less easily carried into the oil 42. Consequently, it is possible to suppress the components of the solution 41 from being mixed in the reaction liquid 47.

When the magnets 71 move in the downward direction in a state in which the magnets 71 are opposed to the plunger 10, the magnetic beads 7 pass through the inside of the cylindrical section 11, exit from the opening on the downstream side of the cylindrical section 11 passing through the front and the back of the ribs 13, and are introduced into the upper syringe 21 of the tube 20. Meanwhile, the magnetic beads 7 pass the interface between the oil 42 and the washing solution 43 in the plunger 10. When the magnetic beads 7 are introduced into the washing solution 43, the nucleic acid binding to the magnetic beads 7 is washed by the washing solution 43.

At this stage, the bar-like section 12 of the plunger 10 is not inserted into the lower syringe 22 of the tube 20. Therefore, when the magnets 71 move from a position opposed to the upper syringe 21 (the height of the upper syringe 21) to a position opposed to the capillary 23 (the height of the capillary 23), the magnetic beads 7 move from the upper syringe 21 to the lower syringe 22 and move from the lower syringe 22 to the capillary 23. The first oil plug 44 is present on the upstream side of the capillary 23. When the magnetic beads 7 move from the lower syringe 22 to the capillary 23, the magnetic beads 7 pass the interface between the washing solution 43 and the oil. At this point, since the washing solution 43 is wiped by the oil, the components of the washing solution 43 are less easily carried into the oil. Consequently, it is possible to suppress the components of the washing solution 43 from being mixed in the washing solution plug 45 and the reaction liquid plug 47.

When the magnets 71 move from a position opposed to the first oil plug 44 (the height of the first oil plug 44) to a position opposed to the washing solution plug 45 (the height of the washing solution plug 45), the magnetic beads 7 pass the interface between the oil and the washing solution 43. When the magnetic beads 7 are introduced into the washing solution plug 45, the nucleic acid binding to the magnetic beads 7 is washed by the washing solution 43.

When the magnets 71 move from a position opposed to the washing solution plug 45 (the height of the washing solution plug 45) to a position opposed to the second oil plug 46 (the height of the second oil plug 46), the washing solution 43 and the magnetic beads 7 pass the interface between the washing solution 43 and the oil. At this point, since the washing solution 43 is wiped by the oil, the components of the washing solution 43 are less easily carried into the oil. Consequently, it is possible to suppress the components of the washing solution 43 from being mixed in the reaction liquid plug 47.

When the magnets 71 move from the position opposed to the second oil plug 46 (the height of the second oil plug 46) to a position opposed to the reaction liquid plug 47 (the height of the reaction liquid plug 47), the magnetic beads 47 pass the interface between the oil and the reaction liquid 47.

The controller 90 controls the heater for elution 65A to heat the reaction liquid plug 47 to about 50° C. before the magnetic beads 7 are introduced into the reaction liquid plug 47. By heating the reaction liquid 47 before the magnetic beads 7 are introduced, it is possible to reduce time until elution of the nucleic acid ends after the magnetic beads 7 are introduced into the reaction liquid 47.

As shown in FIG. 11B, after the magnets 71 move to a position opposed to the reaction liquid plug 47 (the height of the reaction liquid plug 47), the controller 90 stops the motor for lifting and lowering 73B, stops the movement in the up-down direction of the magnets 71, and performs treatment at 50° C. for thirty seconds. Then, the nucleic acid binding to the magnetic beads 7 is isolated into the liquid of the reaction liquid plug 47 and the reverse transcription reaction progresses. By heating the reaction liquid 47, the elution of the nucleic acid from the magnetic beads 7 and the reverse transcription reaction are accelerated.

After eluting the nucleic acid in the reaction liquid plug 47, the controller 90 drives the motor for lifting and lowering 73B in the opposite direction, gradually moves the carriage 73A in the upward direction, and gradually moves the magnets 71 in the upward direction. The controller 90 moves the carriage 73A in the upward direction at speed for allowing the magnetic beads 7 to move together with the magnets 71.

When the magnets 71 move in the upward direction in the state shown in FIG. 11B, the magnetic beads 7 move from the reaction liquid plug 47 to the second oil plug 46. The magnetic beads 7 are removed from the reaction liquid plug 47.

When the magnets 71 gradually move to a position opposed to the upper syringe 21, the magnetic beads 7 also move to the upper syringe 21. The magnetic beads 7 are present on the upper side than the lower syringe 22. If the magnetic beads 7 are moved to this position, the magnetic beads 7 are not introduced into the PCR container 30 when the plunger 10 is pushed. Therefore, between this state and the stage shown in FIG. 11C, the controller 90 may move the carriage 73A in the upward direction at speed for not allowing the magnetic beads 7 to follow the movement of the magnets 71. If the magnetic beads 7 are not introduced into the PCR container 30 when the plunger 10 is pushed, the moving speed of the carriage 73A may be increased at an earlier stage.

Information concerning the moving speed of the magnets 71 is stored in the storage device of the controller 90. The controller 90 executes the operation explained above (the operation for moving the magnets 71 up and down) according to the information.

Swing of the Magnets 71

While moving the magnets 71 in the up-down direction, the controller 90 may drive the motor for swinging 75A and swing the pair of magnets 71, which hold the cartridge 1, in the front-back direction.

Figure 12:
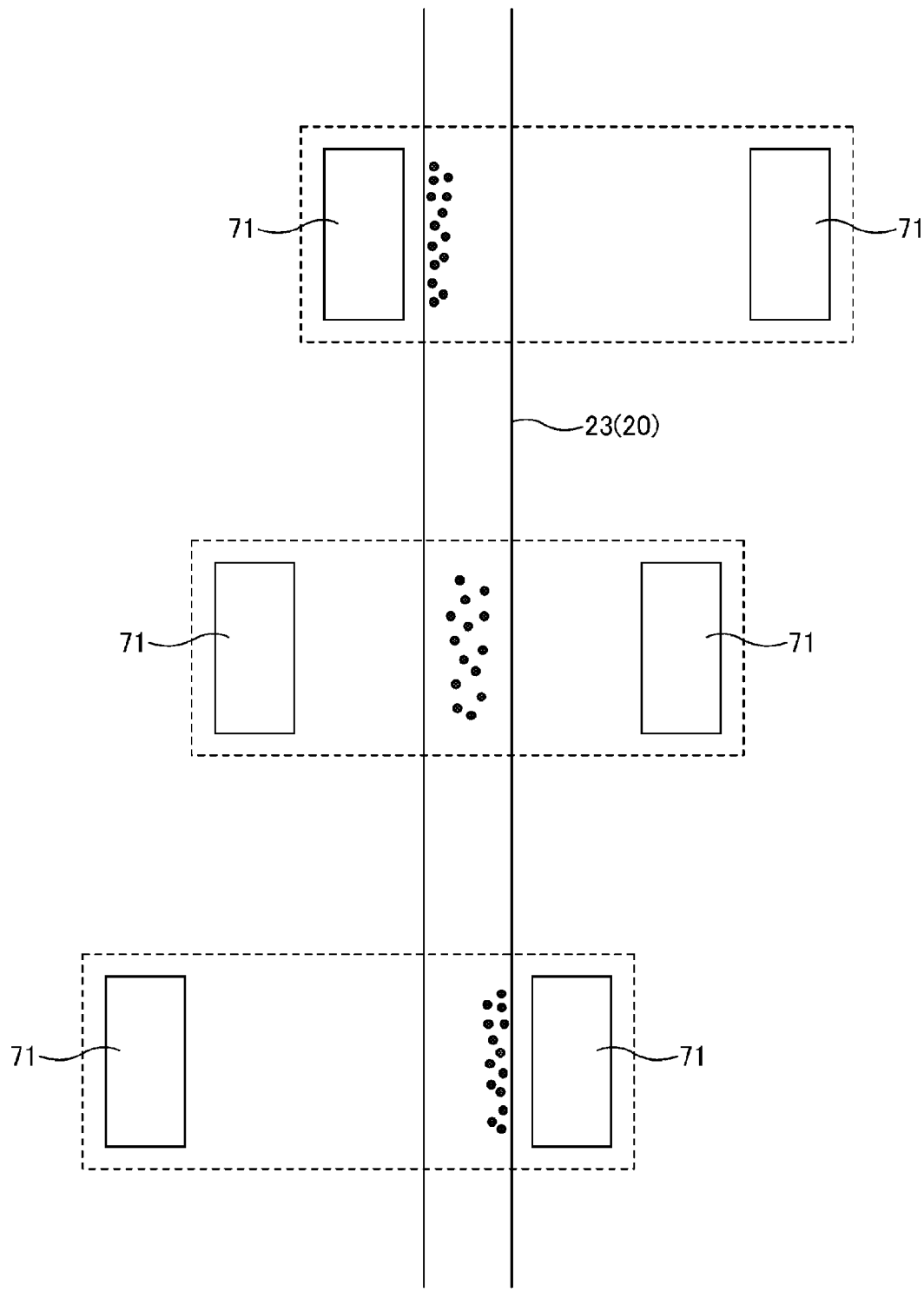
FIG. 12 is a conceptual diagram of the behavior of the magnetic beads at the time when the magnets are swung.

FIG. 12 is a conceptual diagram of the behavior of the magnetic beads 7 at the time when the magnets 71 are swung.

While the magnets 71 move in the up-down direction, the tube 20 is placed between the pair of magnets 71 in the front-back direction. Since the pair of magnets 71 is retained by the arm 72, the distance in the front-back direction between the pair of magnets 71 is substantially fixed. Therefore, when one of the pair of magnets 71 approaches the tube 20, the other separates from the tube 20.

The magnetic beads 7 are attracted to the magnet 71 closer to the tube 20. Therefore, when one magnet 71 is close to the tube 20, the magnetic beads 7 are attracted to the side of the magnet 71. Thereafter, when the magnet 71 separates from the tube 20 and the magnet 71 on the opposite side approaches the tube 20, the magnetic beads 7 are attracted to the magnet 71 on the opposite side. Consequently, the magnetic beads 7 move in the front-back direction. When the pair of magnets 71 is swung in the front-back direction, the magnetic beads 7 move back and forth in the front-back direction.

When the magnetic beads 7 move back and forth in the front-back direction, liquid easily comes into contact with the magnetic beads 7. In particular, since the liquid in the capillary 23 hardly has fluidity, when it is desired to bring the liquid in the capillary 23 into contact with the magnetic beads 7 as much as possible, it is effective to move the magnetic beads 7 back and forth in the front-back direction.

FIG. 13 is a table showing presence or absence of the swing of the magnets 71.

When the magnetic beads 7 move in the downward direction in the oil plug (the first oil plug 44 or the second oil plug 46), the controller 90 stops a swinging motor not to swing the magnets 71. At this point, the controller 90 moves the magnets 71 in the downward direction in a state in which one of the pair of magnets 71 is brought close to the tube 20. This is because the magnetic beads 7 easily follow the movement of the magnets 71 compared with the time when the distances between the magnets 71 and the tube 20 are equal.

When the magnetic beads 7 move in the downward direction in the washing solution plug 45, the controller 90 drives the swinging motor to swing the magnets 71 in the front-back direction. Consequently, since the magnetic beads 7 move in the downward direction while swinging in the washing solution plug 45 in the front-back direction, it is possible to improve washing efficiency of the magnetic beads 7. Since the washing efficiency is improved, it is possible to suppress an amount of the washing solution plug 45 and attain a reduction in the size of the cartridge 1.

When the magnetic beads 7 pass the interface between the washing solution 43 and the oil (the second oil plug 46), the controller 90 stops the swinging motor not to swing the magnet 71. Consequently, since the magnetic beads 7 pass the interface without swinging, the components of the washing solution 43 are less easily carried into the oil. The controller 90 moves the magnets 71 in the downward direction in a state in which one of the pair of magnets 71 is brought close to the tube 20. Consequently, the magnetic beads 7 are attracted to the magnet 71 closer to the tube 20 and condense. The washing solution 43 adhering to the magnetic beads 7 is reduced. Therefore, the components of the washing solution 43 are less easily carried into the oil.

When the magnetic beads 7 are present in the reaction liquid plug 47, the controller 90 drives the swinging motor to swing the magnets 71 in the front-back direction. Consequently, the magnetic beads 7 swing in the front-back direction in the reaction liquid plug 47. Therefore, it is possible to improve elution efficiency of the nucleic acid binding to the magnetic beads 7. Since the elution efficiency is improved, it is possible to reduce time until the elution of the nucleic acid is finished after the magnetic beads 7 are introduced into the reaction liquid 47.

After the nucleic acid is eluted in the reaction liquid plug 47, when the magnets 71 are moved in the upward direction to lift the magnetic beads 7, the controller 90 stops the swinging motor not to swing the magnets 71. At this point, the controller 90 moves the magnets 71 in the downward direction in a state in which one of the pair of magnets 71 is brought close to the tube 20. Consequently, the magnetic beads 7 easily follow the movement of the magnet 71. It is possible to increase moving speed of the magnets 71.

In the storage device of the controller 90, information concerning the positions of the plugs of the capillary 23 and swing information shown in FIG. 13 are stored. The controller 90 executes the operation explained above (the operation for swinging the magnets 71) according to the information.

(3) Droplet Formation Treatment

Figure 14A:
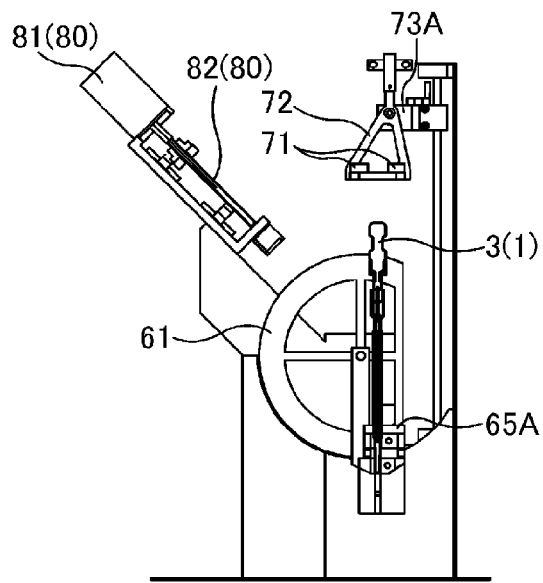
FIGS. 14A to 14C are explanatory diagrams of droplet formation treatment.
Figure 14B:
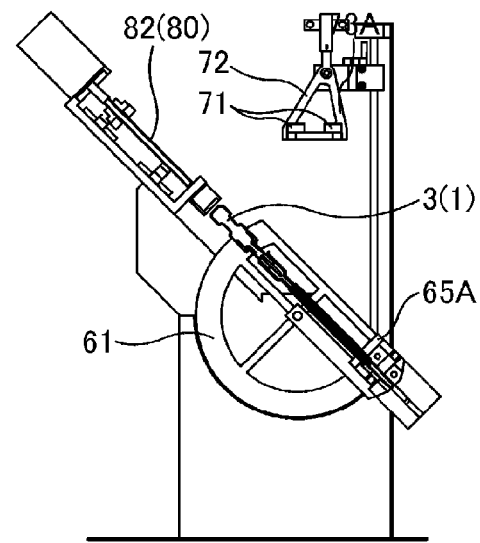
Figure 14C:
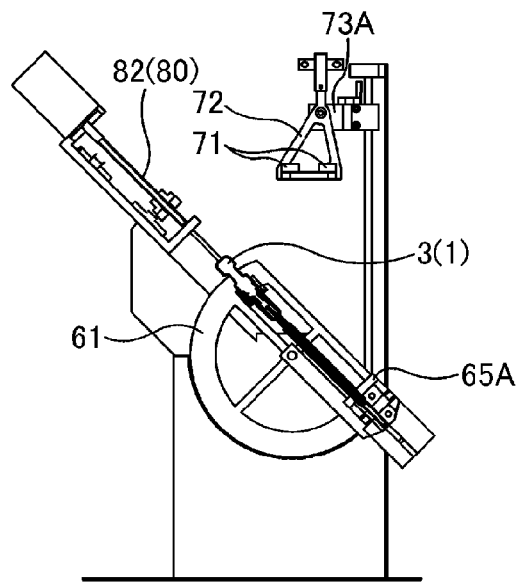

FIGS. 14A to 14C are explanatory diagrams of droplet formation treatment. FIG. 14A is an explanatory diagram of a state of the PCR apparatus 50 at the time when the magnets 71 are lifted. FIG. 14B is an explanatory diagram of a state in which the rotating body 61 is rotated 45 degrees. FIG. 14C is an explanatory diagram of a state in which the rod 82 of the pressing mechanism 80 pushes the plunger 10.

As shown in FIG. 14A, when the carriage 73A is present in the retracted position, even if the cartridge 1 rotates, the lifting and lowering mechanism 73 does not come into contact with the cartridge 1. In such a state, the controller 90 rotates the rotating body 61 45 degrees.

As shown in FIG. 14B, when the rotating body 61 rotates 45 degrees, the longitudinal direction of the cartridge 1 is parallel to the moving direction of the rod 82 of the pressing mechanism 80. The controller 90 drives the plunger motor 81 to move the rod 82. When the rod 82 comes into contact with the attachment stand 11A of the plunger 10 of the cartridge 1 and then further moves, the plunger 10 is pushed in to the tube 20 side. The controller 90 moves the rod 82 to a state shown in FIG. 14C and pushes the plunger 10 until the attachment stand 11A of the plunger 10 comes into contact with the upper edge of the tube 20.

When the plunger 10 is pushed in to the tube 20 side, the seal 12A of the bar-like section 12 of the plunger 10 fits in the lower syringe 22 of the tube 20 (see FIG. 2B). When the plunger 10 is further pushed in, the seal 12A slides in the lower syringe 22. Consequently, the liquid (the third oil plug 48, the reaction liquid plug 47, etc.) on the downstream side of the tube 20 is pushed out to the channel forming section 35 of the PCR container 30 by a distance equivalent to the volume of the sliding of the seal 12A in the lower syringe 22.

First, the third oil plug 48 of the tube 20 flows into the channel forming section 35. Since the oil is filled in the channel forming section 35, the oil equivalent to the third oil plug 48 flowing into the channel forming section 35 flows into the oil reception space 32A from the channel forming section 35. The oil interface of the oil reception space 32A rises. At this point, the pressure of the liquid in the channel forming section 35 rises to be higher than the outside pressure (the pressure of the oil reception space 32A) because of a pressure loss of the lower seal section 34B. After the third oil plug 48 is pushed out from the tube 20, the reaction liquid plug 47 flows into the channel forming section 35 from the tube 20. Since the inner diameter of the channel forming section 35 is larger than the inner diameter of the capillary 23, the reaction liquid 47 having a plug shape in the tube 20 changes to a droplet shape in the oil in the channel forming section 35.

The volume of the sliding of the seal 12A in the lower syringe 22 (an amount of the liquid in the tube 20 pushed out from the downstream side) is larger than a total amount of the reaction liquid plug 47 and the third oil plug 48 in the tube 20. Therefore, after the reaction liquid plug 47 is pushed out from the tube 20, a part of the second oil plug 46 is also pushed out to the channel forming section 35. Consequently, the reaction liquid 47 does not remain in the tube 20. All the liquid of the reaction liquid plug 47 changes to a droplet shape. Since a part of the second oil plug 46 is pushed out from the downstream side of the tube 20, the droplet-like reaction liquid 47 easily separates from the tube 20 (the droplet-like reaction liquid 47 less easily adheres to the opening of the capillary 23).

The inner diameter of the end of the capillary 23 (the opening diameter of the capillary 23) is designed relatively small. Therefore, the reaction liquid 47 changed to the droplets in the PCR container 30 less easily adheres to the opening of the capillary 23. The reaction liquid 47 has specific gravity larger than the specific gravity of the oil in the PCR container 30. Therefore, the droplet-like reaction liquid 47 separates from the end of the capillary 23 and precipitates toward the bottom 35A flowing through the channel forming section 35. However, at this stage, since a channel of the channel forming section 35 tilts at 45 degrees, the droplet-like reaction liquid 47 easily adheres to the inner wall of the channel forming section 35. Therefore, it is necessary to return the channel of the channel forming section 35 to the vertical direction.

After the droplet-like reaction liquid 47 is formed (after the plunger 10 is pushed), the controller 90 drives the plunger motor 81 in the opposite direction and returns the rod 82 to the original position. In this state, even if the cartridge 1 rotates, the rod 82 of the pressing mechanism 80 does not come into contact with the cartridge 1. In such a state, the controller 90 returns the rotating body 61 to the reference position. When the rotating body 61 is returned to the reference position, the channel of the channel forming section 35 changes to the vertical direction. Therefore, the droplet-like reaction liquid 47 less easily adheres to the inner wall of the channel forming section 35.

(4) Heat Cycle Treatment

FIGS. 15A to 15D are explanatory diagrams of the heat cycle treatment. FIGS. 15A and 15B are an explanatory diagram of a state in which temperature treatment on a low temperature side is applied to the reaction liquid 47. FIGS. 15C and 15D are an explanatory diagram of a state in which temperature treatment on a high temperature side is applied to the reaction liquid 47. States of the PCR apparatus 50 are shown on the left sides of the figures. States of the inside of the channel forming section 35 of the PCR container 30 are shown on the right sides of the figures.

When the cartridge 1 is fixed in the normal position with respect to the mounting section 62, the upstream side (the high-temperature region 36A) of the channel forming section 35 of the PCR container 30 is opposed to the high-temperature side heater 65B. The downstream side (the low-temperature region 36B) of the channel forming section 35 of the PCR container 30 is opposed to the low-temperature side heater 65C. During the heat cycle treatment, the controller 90 heats, with the high-temperature side hater 65B provided in the rotating body 61, the liquid in the high-temperature region 36A on the upstream side of the channel forming section 35 of the PCR container 30 to about 90 to 100° C. The controller 90 heats, with the low-temperature side heater 65C provided in the rotating body 61, the liquid in the low-temperature region 36B on the downstream side of the channel forming section 35 to about 50 to 75° C. Consequently, during the heat cycle treatment, a temperature gradient is formed in the liquid in the channel forming section 35 of the PCR container 30. Since the mounting section 62 and the heaters are provided in the rotating body 61, even if the rotating body 61 rotates, the positional relation between the cartridge 1 and the heaters is maintained.

During the heat cycle treatment, the liquid in the PCR container 30 is heated. If the liquid in the PCR container 30 is heated and air bubbles are formed, it is likely that fluctuation occurs in the temperature of the liquid in the channel forming section 35 and movement (precipitation) of the droplet-like reaction liquid 47 in the channel forming section 35 is inhibited. However, in this embodiment, the pressure of the liquid in the channel forming section 35 is higher than the outside pressure because of a pressure loss in the lower seal section 34B, air bubbles are less easily formed in the liquid in the PCR container 30.

As shown in FIGS. 15A and 15B, when the rotating body 61 is present in the reference position, the low-temperature side heater 65C is located on the lower side of the high-temperature side heater 65B. The bottom 35A of the PCR container 30 of the cartridge 1 is directed downward. Since the droplet-like reaction liquid 47 has specific gravity larger than the specific gravity of the oil, the droplet-like reaction liquid 47 precipitates in the channel forming section 35. When the droplet-like reaction liquid 47 precipitates in the channel forming section 35, the droplet-like reaction liquid 47 reaches the bottom 35A of the PCR container 30, ends the precipitation in the bottom 35A, and stays in the low-temperature region 36B. Consequently, the droplet-like reaction liquid 47 moves to the low-temperature region 36B. The controller 90 retains a state shown in FIG. 15B for a predetermined time and heats the droplet-like reaction liquid 47 at about 50 to 75° C. in the low-temperature region 36B (applies the temperature treatment on the low temperature side). During the heating, extension reaction of the polymerase reaction occurs.

When the controller 90 drives the motor for rotation 66 to rotate the rotating body 61 180 degrees in the state shown in FIG. 15A, the state changes to a state shown in FIG. 15C. When the rotating body 61 rotates 180 degrees from the reference position, the cartridge 1 is vertically reversed. The high-temperature side heater 65B and the low-temperature side heater 65C are also vertically reversed. That is, the high-temperature side heater 65B is located on the lower side of the low-temperature side heater 65C. The bottom 35A of the PCR container 30 of the cartridge 1 is directed upward. When the droplet-like reaction liquid 47 precipitates in the channel forming section 35, the droplet-like reaction liquid 47 reaches the end of the tube 20 (the end of the capillary 23), ends the precipitation at the end of the tube 20, and stays in the high-temperature region 36A shown in FIG. 15D. Consequently, the droplet-like reaction liquid 47 moves to the high-temperature region 36A. The controller 90 retains the state shown in FIG. 15C for a predetermined time and heats the droplet-like reaction liquid 47 to about 90 to 100° C. in the high-temperature region 36A (applies the temperature treatment on the high temperature side). During the heating, denaturation reaction of the polymerase reaction occurs.

When the controller 90 drives the motor for rotation 66 to rotate the rotating body 61 −180 degrees in the state shown in FIG. 15C, the state returns to the state shown in FIG. 15A. In this state, when the droplet-like reaction liquid 47 precipitates in the channel forming section 35, the droplet-like reaction liquid 47 moves to the low-temperature region 36B and is heated to about 50 to 75° C. again in the low-temperature region 36B (subjected to the temperature treatment on the low temperature side), as shown in FIG. 15B. Since the inner diameter of the end of the capillary 23 (the opening diameter of the capillary 23) is designed relatively small, the reaction liquid 47 less easily adheres to the opening of the capillary 23. Therefore, when the rotating body 61 rotates −180 degrees in the state shown in FIG. 15C, the droplet-like reaction liquid 47 separates from the tube 20 and precipitates toward the bottom 35A of the PCR container 30 without adhering to the opening of the capillary 23.

The controller 90 repeatedly drives the motor for rotation 66 to change the rotating position of the rotating body 61 to the state shown in FIG. 15A and the state shown in FIG. 15C at a predetermined cycle number. Consequently, the PCR apparatus 50 can apply the heat cycle treatment of PCR to the reaction liquid 47.

The storage device of the controller 90 stores heat cycle information such as the temperature of the high-temperature side heater 65B, the temperature of the low-temperature side heater 65C, time of retention of the state shown in FIG. 15A, time of retention of the state shown in FIG. 15C, and a cycle number (the number of times of repetition of the state shown in FIG. 15A and the state shown in FIG. 15C). The controller 90 executes the treatment explained above according to the heat cycle information.

(5) Fluorescence Measurement

FIGS. 16A and 16B is a first explanatory diagram of fluorescence measurement during the rotation of the rotating body 61. FIGS. 16C and 16D is a second explanatory diagram of the fluorescence measurement during the rotation of the rotating body 61. FIGS. 17A and 17B is a third explanatory diagram of the fluorescence measurement during the rotation of the rotating body 61. FIGS. 17C and 17D is a fourth explanatory diagram of the fluorescence measurement during the rotation of the rotating body 61. As explained above, the fluorescence measuring device 55 is fixed to the mounting section 62 of the rotating body 61. The fluorescence measuring device 55 is always opposed to the bottom 35A of the PCR container 30 of the cartridge 1.

In the first embodiment, the fluorescence measurement is performed while rotating the rotating body 61 between a reference position at 0 degree (FIGS. 16A and 16B) and a position at 90 degrees (FIGS. 17A and 17B). That is, the rotation of the rotating body 61 is started in the state shown in FIG. 16A and, at the same time, the fluorescence measurement by the fluorescence measuring device 55 is started. As shown in FIGS. 16C and 16D, the fluorescence measurement is performed even during the rotation of the rotating body 61.

This is because, as shown in FIGS. 17A and 17B, before the rotating body 61 reaches 90 degrees, since the reaction liquid 47 remains precipitating in the bottom 35A, in the PCR apparatus 50 in the first embodiment in which the fluorescence measuring device 55 rotates together with the rotating body 61, the fluorescence measurement can be performed even during the rotation of the rotating body 61. As shown in FIGS. 17C and 17D, when the rotating body 61 rotates to a position exceeding 90 degrees, the reaction liquid 47 starts movement toward the rotation axis side.

In this way, the measurement of fluorescence intensity of the reaction liquid 47 is performed while rotating the rotating body 61. Therefore, it is unnecessary to stop the rotating body 61 while the measurement of the fluorescence intensity is performed. That is, in the PCR apparatus 50 in the first embodiment, by rotating the rotating body 61, the reaction liquid 47 is moved to the high-temperature region 36A and the low-temperature region 36B and predetermined heat cycle is applied to the reaction liquid 47. However, since the fluorescence measurement can be performed during the rotation of the rotating body 61, time necessary for the fluorescence measurement can be included in time of the rotation of the rotating body 61. When the real-time PCR is performed, it is possible to reduce time per cycle of the heat cycle.

In a process for providing the heat cycle, the rotating body 61 is rotated. However, immediately after the rotating body 61 is rotated 180 degrees and moved to the reference position (FIG. 16A) in the state shown in FIG. 15C, in some case, the droplet-like reaction liquid 47 is moving in the channel forming section 35 of the PCR container 30 and has not reached the bottom 35A of the PCR container 30.

Therefore, the controller 90 stops the rotation of the rotating body 61 until a predetermined time elapses after the rotating position of the rotating body 61 changes to the state shown in FIG. 16A (time necessary for the reaction liquid 47 to precipitate in the bottom 35A and for the extension reaction of the polymerase reaction to occur elapses). After the predetermined time elapses, the controller 90 resumes the rotation of the rotating body 61 and causes the fluorescence measuring device 55 to start measurement of fluorescence intensity (FIG. 16A). Consequently, it is possible to perform the fluorescence measurement of the reaction liquid 47 with the fluorescence measuring device 55 after the extension reaction of the polymerase reaction is performed.

As explained above, the PCR apparatus 50, which is the nucleic acid amplification reaction apparatus, includes the rotating body 61 including the mounting section (the fixing section 63 and the insertion hole 64A), on which the cartridge 1 is mounted, and the heaters for PCR (the high-temperature side heater 65B and the low-temperature side heater 65C) that form a temperature gradient on the inside of the PCR container 30, which is the nucleic acid amplification reaction container. The cartridge 1 mounted on the rotating body 61 includes the tube 20 including the reaction liquid plug 47 containing eluate and the PCR container 30 including the oil. In the PCR apparatus 50, the rotating body 61 rotates and the posture of the cartridge 1 changes, whereby the droplet-like reaction liquid 47 introduced from the tube 20 moves on the inside of the PCR container 30. Consequently, the posture of the PCR container 30 changes together with the tube 20 in which the nucleic acid elution treatment is performed. The polymerase reaction can be performed. Therefore, it is possible to reduce a treatment time.

With the PCR apparatus 50 explained above, the rotation axis of the rotating body 61 is located closer to the tube 20 than the PCR container 30 of the cartridge 1. Consequently, the rotating body 61 can be reduced in size. Since the tube 20 is longer than the PCR container 30, if the center of the PCR container 30 is set as a rotation axis, the rotating body 61 is increased in size.

The fixing section 63 that fixes the tube 20 of the cartridge 1 and the insertion hole 64A that fixes the PCR container 30 function as the mounting section that mounts the cartridge 1 on the rotating body 61. Consequently, the long cartridge 1 including the tube 20 and the PCR container 30 is stably fixed.

In the PCR apparatus 50, the heaters for PCR (the high-temperature side heater 65B and the low-temperature side heater 65C) are provided in the rotating body 61. Consequently, irrespective of the rotating position of the rotating body 61, the positional relation between the PCR container 30 of the cartridge 1 and the heaters for PCR is maintained. The temperature gradient formed on the inside of the PCR container 30 is stabilized.

In the PCR apparatus 50, the heater for elution 65A is provided. Consequently, isolation of the nucleic acid from the magnetic beads 7 is accelerated.

The PCR apparatus 50 includes the magnet moving mechanism 70 (the lifting and lowering mechanism 73) that moves the magnets 71 along the tube 20. Consequently, it is possible to automate the movement of the magnetic beads 7, which are the nucleic acid binding solid-phase carrier, and move the magnetic beads 7 in the same manner every time.

The magnet moving mechanism 70 includes the swinging mechanism 75. Consequently, it is possible to adjust condensation and diffusion of the magnetic beads 7 on the inside of the tube 20. It is possible to improve the washing efficiency and the elution efficiency. Further, it is possible to reduce the treatment time.

The PCR apparatus 50 includes the pressing mechanism 80 that pushes the plunger 10 of the cartridge 1. Consequently, it is possible to automate treatment for introducing the reaction liquid plug 47, in which the nucleic acid is eluted, into the PCR container 30 from the tube 20.

Second Embodiment

In a second embodiment, the cartridge 1 having a configuration different from the configuration in the first embodiment is mounted on the PCR apparatus 50.

Cartridge 1

Figures 18A, 18B:
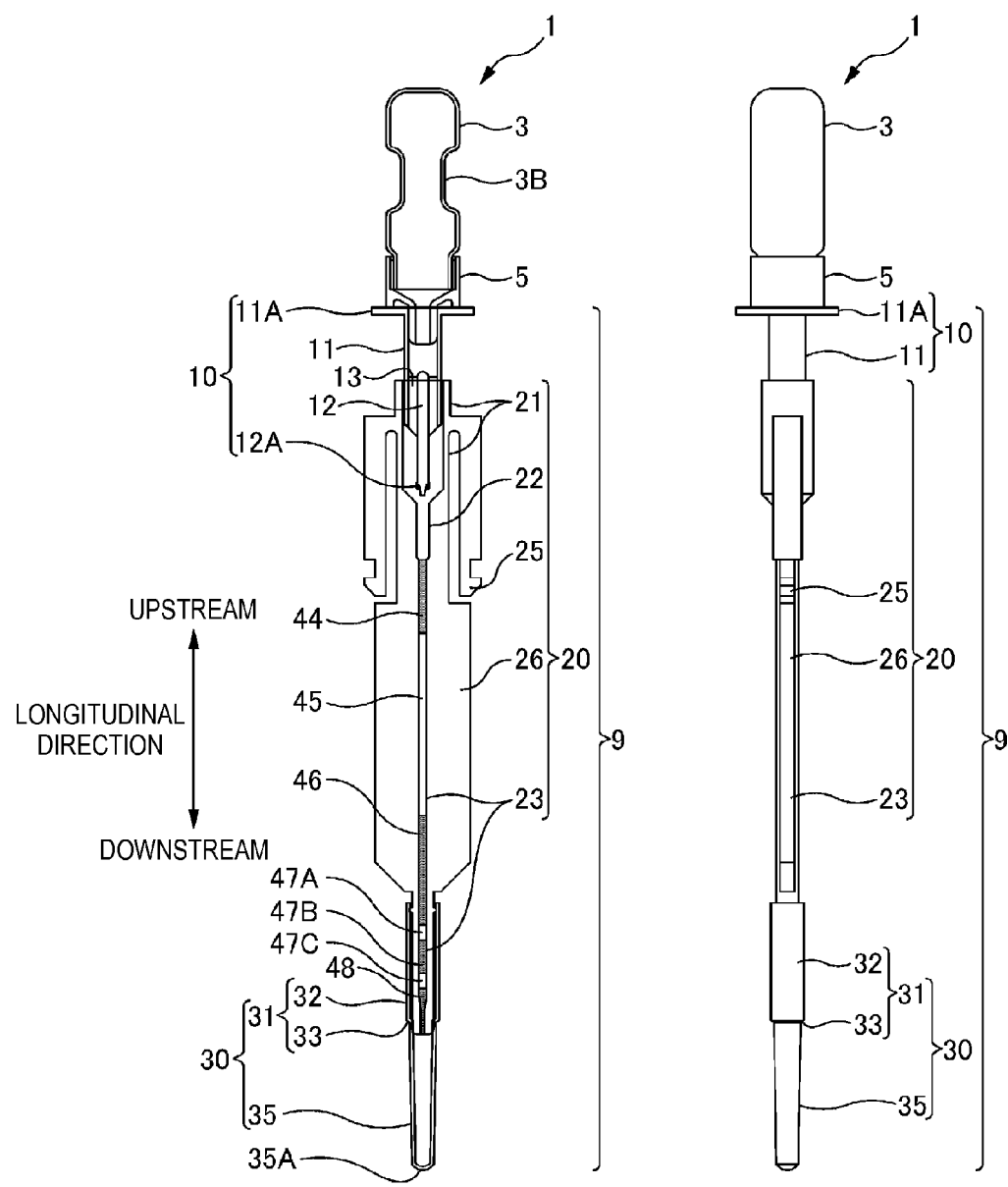
FIGS. 18A and 18B are explanatory diagrams of the cartridge in a second embodiment.
Figure 19C:
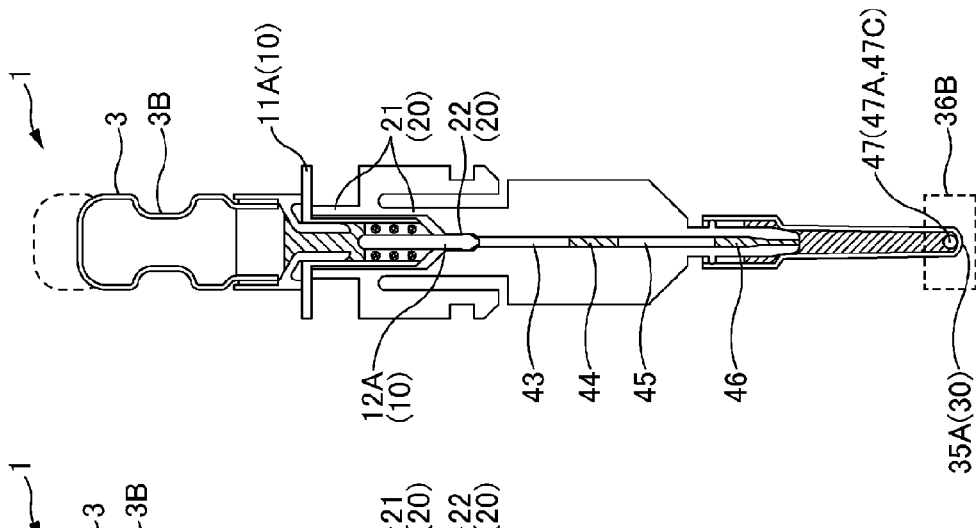
FIG. 19C is an explanatory diagram of the cartridge in the second embodiment after the plunger is pushed.
Figure 19B:
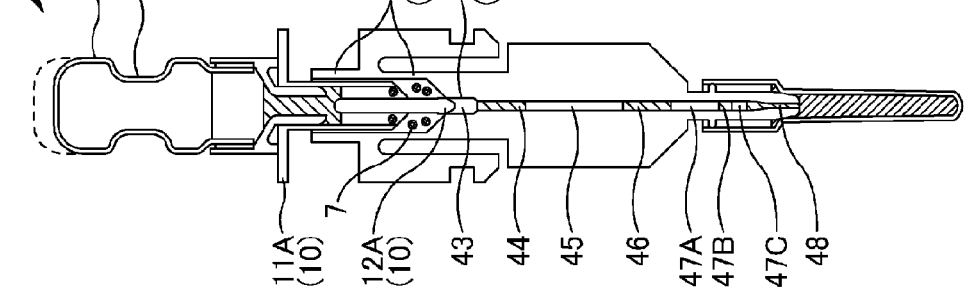
FIG. 19B is a side view of the cartridge in which a plunger is pushed in a state shown in FIG. 19A and a seal comes into contact with a lower syringe.
Figure 19A:
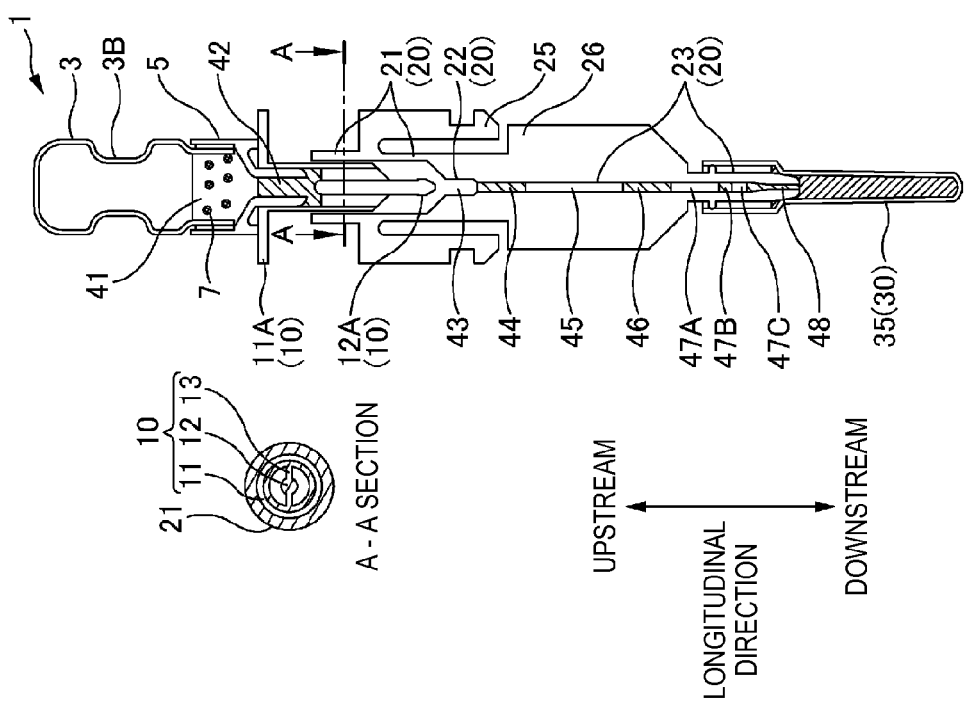
FIG. 19A is an explanatory diagram of an initial state of the cartridge in the second embodiment.

FIGS. 18A and 18B are explanatory diagrams of the cartridge 1 in the second embodiment. FIG. 19A is an explanatory diagram of an initial state of the cartridge 1 in the second embodiment. FIG. 19B is a side view of the cartridge 1 in which the plunger 10 is pushed in a state shown in FIG. 19A and the seal 12A comes into contact with the lower syringe 22. FIG. 19C is an explanatory diagram of the cartridge 1 in the second embodiment after the plunger 10 is pushed. The tube 20 of the cartridge 1 in the second embodiment includes an eluate plug 47A, an oil plug 47B, and a nucleic acid amplification reaction liquid plug 47C instead of the reaction liquid plug 47 in the first embodiment. The oil plug 47B prevents the eluate plug 47A and the nucleic acid amplification reaction liquid plug 47C, which are water-soluble plugs on both sides of the oil plug 47B, from being mixed with each other.

The cartridge 1 is a container for performing nucleic acid elution treatment for eluting nucleic acid from the magnetic beads 7 bound with the nucleic acid and is a container for applying heat cycle treatment for polymerase reaction to a PCR solution, which is mixed liquid of the eluate 47A and the nucleic acid amplification reaction liquid 47C.

The shapes of the tank 3 and the cartridge main body 9 of the cartridge 1 are the same as those in the first embodiment. The solution 41 in the tank 3 of the cartridge 1 is also the same as that in the first embodiment. The oil 42, the first washing solution 43, the first oil plug 44, the washing solution plug 45 (the second washing solution), and the second oil plug 46 in the cartridge main body 9 are also the same as those in the first embodiment. Therefore, explanation thereof is omitted.

The eluate plug 47A and the nucleic acid amplification reaction liquid plug 47C include, for example, reaction liquids shown in the table blow.

Figure 20A:
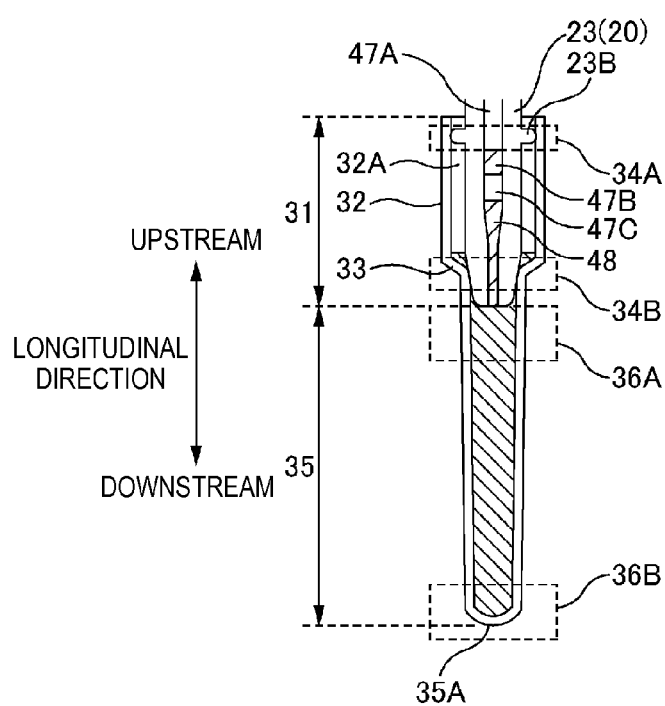
FIGS. 20A and 20B are explanatory diagrams of the periphery of the PCR container in the second embodiment.
Figure 20B:
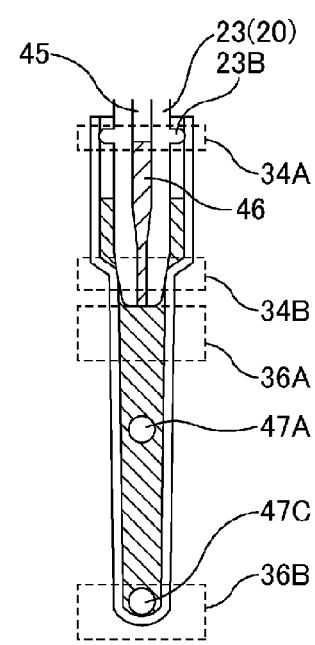

FIG. 20B is an explanatory diagram of a state after the plunger 10 is pressed. FIGS. 19A to 19C are also referred to in the following explanation.

The PCR container 30 is a container that receives liquid pushed out from the tube 20 and is a container that stores a PCR solution, which is mixed liquid of the nucleic acid amplification reaction liquid 47C and the eluate 47A, during heat cycle treatment.

When the plunger 10 is pushed, first, the third oil plug 48 of the tube 20 flows into the channel forming section 35. The oil equivalent to the third oil plug 48 flowing into the channel forming section 35 flows into the oil reception space 32A from the channel forming section 35. The oil interface of the oil reception space 32A rises. At this point, the pressure of the liquid in the channel forming section 35 rises because of a pressure loss of the lower seal section 34B.

After the third oil plug 48 is pushed out from the tube 20, the nucleic acid amplification reaction liquid plug 47C flows into the channel forming section 35 from the tube 20. Since the inner diameter of the channel forming section 35 is larger than the inner diameter of the capillary 23, the nucleic acid amplification reaction liquid 47C having a plug shape (a columnar shape) in the tube 20 changes to a droplet shape in the oil in the channel forming section 35. Since the nucleic acid amplification reaction liquid 47C has specific gravity larger than the specific gravity of the oil, the nucleic acid amplification reaction liquid 47C changed to the droplet shape precipitates.

| | Reagent | Added amount (uL) | Concentration | Final Concentration | Unit |
|---|---|---|---|---|---|
| Eluate | AMV reverse transcription enzyme (Nippon Gene) | 0.2 | 20.0 | 0.1 | units/uL |
| | dNTP | 1.6 | 10.0 | 0.8 | mM |
| | buffer * | 4.0 | | 2.0 | |
| | primer R | 1.0 | 10.0 | 0.5 | uM |
| | BSA | 2.0 | 20.0 | 1.0 | mg/mL |
| | DW | 11.2 | | 5.6 | |
| Nucleic acid amplification reaction liquid | Gane Taq NT PCR enzyme (Nippon Gene) | 0.2 | 5.0 | 0.1 | units/uL |
| | dNTP | 1.0 | 10.0 | 0.5 | mM |
| | buffer * | 4.0 | | 2.0 | |
| | primer F | 1.0 | 10.0 | 0.5 | uM |
| | primer R | 1.0 | 10.0 | 0.5 | uM |
| | probe(Taq man) | 0.4 | 12.5 | 0.2 | uM |
| | BSA | 2.0 | 20.0 | 1.0 | mg/mL |
| | DW | 8.4 | | | |

The eluate refers to liquid for eluting nucleic acid, which adheres to a nucleic acid binding solid-phase carrier, from the carrier into the liquid and performing reverse transcription reaction. Therefore, the eluate 47A is prepared in advance such that the eluate 47A after the elution of the nucleic acid changes to a buffer solution directly used for the revere transcription reaction. The nucleic acid amplification reaction liquid refers to liquid for performing polymerase reaction.

A downstream section of the capillary 23 is inserted into the PCR container 30. Consequently, it is possible to introduce the nucleic acid amplification reaction liquid 47C and the eluate 47A into the PCR container 30 by pushing out the nucleic acid amplification reaction liquid plug 47C and the eluate plug 47A in the tube 20 from the tube 20.

FIGS. 20A and 20B are explanatory diagrams of the periphery of the PCR container 30 in the second embodiment. FIG. 20A is an explanatory diagram of an initial state.

After the nucleic acid amplification reaction liquid plug 47C is pushed out from the tube 20, the oil plug 47B flows into the channel forming section 35. After the oil plug 47B is pushed out from the tube 20, the eluate plug 47A flows into the channel forming section 35 from the tube 20. Since the inner diameter of the channel forming section 35 is larger than the inner diameter of the capillary 23, the eluate 47A having a plug shape (a columnar shape) in the tube 20 changes to a droplet shape in the oil in the channel forming section 35. Since the eluate 47A has specific gravity larger than the specific gravity of the oil, the eluate 47A changed to the droplet shape precipitates. When the eluate t 47A changed to the droplet shape precipitates, the droplet-like eluate 47A joins with the droplet-like nucleic acid amplification reaction liquid 47C, which has already precipitated in the bottom of the channel forming section 35, in the oil and changes to the droplet-like PCR solution 47.

Explanation of the Operation of the PCR Apparatus 50

The structure of the PCR apparatus 50 in the second embodiment is the same as that in the first embodiment.

Therefore, explanation is omitted concerning the structure (the rotating mechanism 60, the magnet moving mechanism 70, the pressing mechanism 80, the fluorescence measuring device 55, the controller 90, etc.) of the PCR apparatus 50. The operation of the PCR apparatus 50 performed when the cartridge 1 in the second embodiment is mounted is explained.

(1) Mounting Operation of the Cartridge 1

States during the mounting of the cartridge 1 in the second embodiment are the same as those shown in FIGS. 9A to 9D in the first embodiment. In the second embodiment, as shown in FIG. 9C, when the cartridge 1 is fixed to a normal position with respect to the mounting section 62, the eluate plug 47A of the tube 20 is opposed to the heater for elution 65A (on the other hand, in the first embodiment, the reaction liquid plug 47 of the tube 20 is opposed to the heater for elution 65A).

(2) Nucleic Acid Elution Treatment

States during nucleic acid elution treatment in the second embodiment are the same as those shown in FIGS. 11A to 11C in the first embodiment.

In the second embodiment, as shown in FIG. 11B, after the magnets 71 move to a position opposed to the eluate plug 47A (the height of the eluate plug 47A), the controller 90 stops the motor for lifting and lowering 73B, stops the movement in the up-down direction of the magnets 71, and performs treatment at 50° C. for thirty seconds. Then, the nucleic acid binding to the magnetic beads 7 is isolated into the liquid of the eluate plug 47A and the reverse transcription reaction progresses. By heating the eluate plug 47A, the elution of the nucleic acid from the magnetic beads 7 and the reverse transcription reaction are accelerated.

After eluting the nucleic acid in the eluate plug 47A, the controller 90 drives the motor for lifting and lowering 73B in the opposite direction, gradually moves the carriage 73 in the upward direction, and gradually moves the magnets 71 in the upward direction. When the magnets 71 move in the upward direction in the state shown in FIG. 11B, the magnetic beads 7 move from the eluate plug 47A to the second oil plug 46. The magnetic beads 7 are removed from the eluate plug 47A.

In the second embodiment, the magnetic beads 7 do not come into contact with the nucleic acid amplification reaction liquid 47C. Therefore, it is unlikely that an enzyme of the nucleic acid amplification reaction liquid 47C adheres to the magnetic beads 7 and that reaction inhibition occurs. Therefore, in the second embodiment, it is possible to perform the nucleic acid elution treatment under higher efficiency conditions (higher temperature, a higher frequency of swinging, an increase in an amount of magnetic beads, etc.) than in the first embodiment.

(3) Droplet Formation Treatment

States during the droplet formation treatment in the second embodiment are the same as those shown in FIGS. 14A to 14C in the first embodiment.

When the plunger 10 is pushed, first, the third oil plug 48 of the tube 20 flows into the channel forming section 35. The oil equivalent to the third oil plug 48 flowing into the channel forming section 35 flows into the oil reception space 32A from the channel forming section 35. The oil interface of the oil reception space 32A rises. At this point, the pressure of the liquid in the channel forming section 35 rises because of a pressure loss of the lower seal section 34B.

After the third oil plug 48 is pushed out from the tube 20, the nucleic acid amplification reaction liquid plug 47C flows into the channel forming section 35 from the tube 20. Since the inner diameter of the channel forming section 35 is larger than the inner diameter of the capillary 23, the nucleic acid amplification reaction liquid plug 47C having a plug shape (a columnar shape) in the tube 20 changes to a droplet shape in the channel forming section 35. Since the nucleic acid amplification reaction liquid 47C has specific gravity larger than the specific gravity of the oil, the nucleic acid amplification reaction liquid 47C changed to the droplet shape precipitates.

After the nucleic acid amplification reaction liquid plug 47C is pushed out from the tube 20, the oil plug 47B flows into the channel forming section 35. After the oil plug 47B is pushed out from the tube 20, the eluate plug 47A flows into the channel forming section 35 from the tube 20. Since the inner diameter of the channel forming section 35 is larger than the inner diameter of the capillary 23, the eluate 47A having a plug shape (a columnar shape) in the tube 20 changes to a droplet shape in the channel forming section 35. Since the eluate 47A has specific gravity larger than the specific gravity of the oil, the eluate 47A changed to the droplet shape precipitates. When the eluate 47A changed to the droplet shape precipitates, the droplet-like eluate 47A joins with the droplet-like nucleic acid amplification reaction liquid 47C, which has already precipitated in the bottom of the channel forming section 35, in the oil and changes to the droplet-like PCR solution 47.

Since both of the droplet-like affluent 47A and the nucleic acid amplification reaction liquid 47C are small, two droplets sometimes do not join in the bottom of the channel forming section 35 and remain separated from each other. Therefore, after the droplet-like eluate 47A precipitates in the bottom of the channel forming section 35, the controller 90 drives the rotating mechanism 60 little by little and vibrates the rotating body 61. Consequently, even if the two droplets are separated in the bottom of the channel forming section 35, the cartridge 1 vibrates, whereby the two droplets join and change to the droplet-like PCR solution 47. The viscosity of the droplets may be reduced to facilitate the joining of the two droplets by heating the droplets with the high-temperature side heater 65B or the low-temperature side heater 65C.

After the droplet formation treatment, heat cycle treatment and fluorescence measurement are performed. The heat cycle treatment and the fluorescence measurement in the second embodiment are the same as those in the first embodiment. Therefore, explanation thereof is omitted.

In the second embodiment, as in the first embodiment, the PCR apparatus 50 includes the rotating body 61 including the mounting section (the fixing section 63 and the insertion hole 64A), on which the cartridge 1 is mounted, the heaters for PCR (the high-temperature side heater 65B and the low-temperature side heater 65C) that form a temperature gradient on the inside of the PCR container 30, which is the nucleic acid amplification reaction container. The rotating body 61 rotates and the posture of the cartridge 1 changes, whereby the droplet-like reaction liquid 47 introduced from the tube 20 moves on the inside of the PCR container 30. Consequently, the posture of the PCR container 30 changes together with the tube 20 in which the nucleic acid elution treatment is performed. The polymerase reaction can be performed. Therefore, it is possible to reduce a treatment time.

Third Embodiment

Figure 21A:
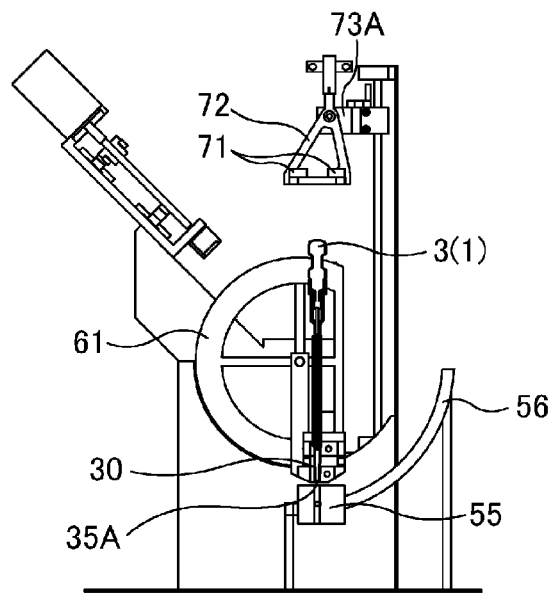
FIGS. 21A and 21B are side views of the main configuration of the PCR apparatus in a third embodiment.
Figure 21B:
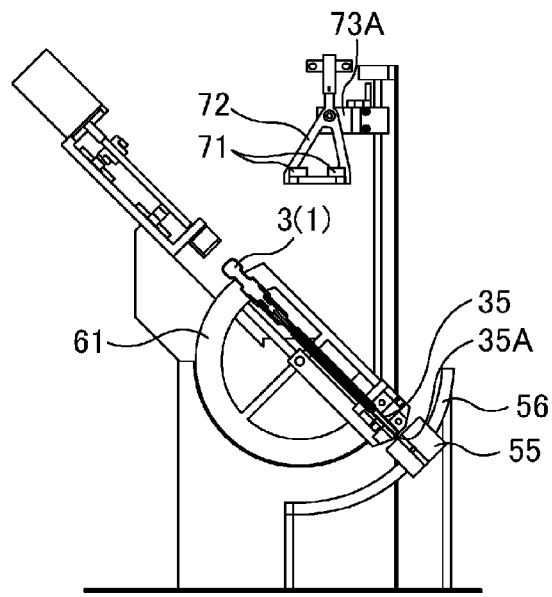

FIGS. 21A and 21B are side views of the main configuration of the PCR apparatus 50 in a third embodiment. In FIGS. 21A and 21B, components having functions same as those in the first embodiment are denoted by reference numerals and signs same as those in the first embodiment. As shown in FIG. 21A, a rotating position of the rotating body 61 at the time when a mounting direction of the mounting section 62 is in the up-down direction is set as a reference (0 degree) and a counterclockwise direction viewed from the right is set as a positive direction to show an angle.

In the first embodiment, the fluorescence measuring device 55 is fixed to the rotating body 61 and the fluorescence measuring device 55 rotates together with the rotation of the rotating body 61. However, in the configuration of the PCR apparatus 50 in the third embodiment, the fluorescence measuring device 55 is not fixed to the rotating body 61 and is separate from the rotating body 61. The fluorescence measuring device 55 moves in synchronization with the rotation of the rotating body 61.

To realize such a configuration, in the PCR apparatus 50 in the third embodiment, a curved guide rail 56 is provided such that the fluorescence measuring device 55 can move along a track of the bottom 35A of the PCR container 30 at the time when the rotating body 61 rotates. The guide rail 56 is provided to draw an arc in a range of about 0 degree to 90 degrees. The fluorescence measuring device 55 is movable along the guide rail 56. Consequently, for example, it is possible to perform the fluorescence measurement for the reaction liquid 47 while rotating the rotating body 61 after the reaction liquid 47 precipitates in the bottom 35A of the PCR container 30 (FIG. 21B).

If the fluorescence measuring device 55 is fixed to the PCR apparatus 50, when the fluorescence measurement is performed, the rotation of the rotating body 61 is temporarily stopped to perform the fluorescence measurement. On the other hand, in the PCR apparatus 50 in the third embodiment, it is possible to perform the fluorescence measurement while rotating the rotating body 61. Further, it is possible to reduce time per cycle of a heat cycle and provide the PCR apparatus 50 with high processing speed.

Fourth Embodiment

Figure 22A:
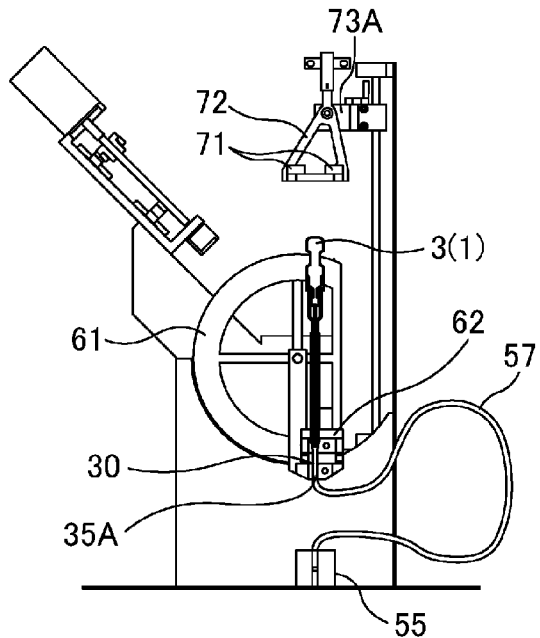
FIGS. 22A and 22B are side views of the main configuration of the PCR apparatus in a fourth embodiment.
Figure 22B:
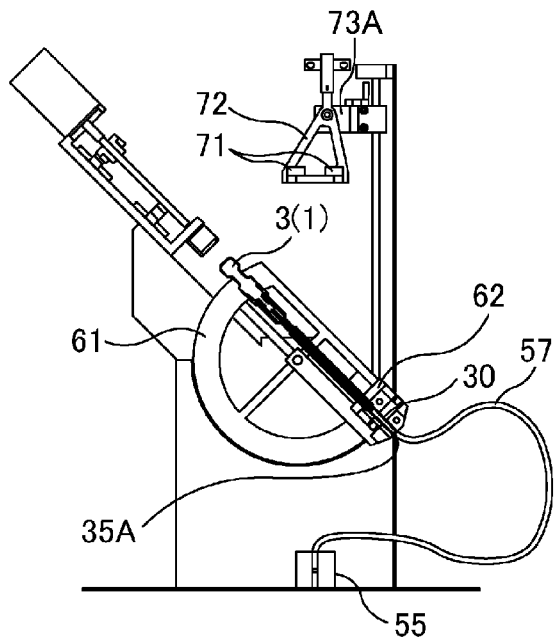

FIGS. 22A and 22B are side views of the main configuration of the PCR apparatus 50 in a fourth embodiment. In FIGS. 22A and 22B, components having functions same as those in the first embodiment are denoted by reference numerals and signs same as those in the first embodiment. As shown in FIG. 22A, a rotating position of the rotating body 61 at the time when a mounting direction of the mounting section 62 is in the up-down direction is set as a reference (0 degree) and a counterclockwise direction viewed from the right is set as a positive direction to show an angle.

In the fourth embodiment, one end of an optical fiber 57 is attached to the fluorescence measuring device 55. On the other hand, the other end of the optical fiber 57 is fixed to the mounting section 62 such that fluorescence measurement for the reaction liquid 47 in the bottom 35A of the PCR container can be performed. To appropriately perform the fluorescence measurement, a lens or the like may be provided on the other end side of the optical fiber 57 fixed to the mounting section 62. The optical fiber 57 has length enough for allowing the rotating body 61 to rotate 360 degrees.

Consequently, it is possible to perform the fluorescence measurement while rotating the rotating body 61. Further, it is possible to reduce time per cycle of a heat cycle and provide the PCR apparatus 50 with high processing speed.

Fifth Embodiment

Figure 23A:
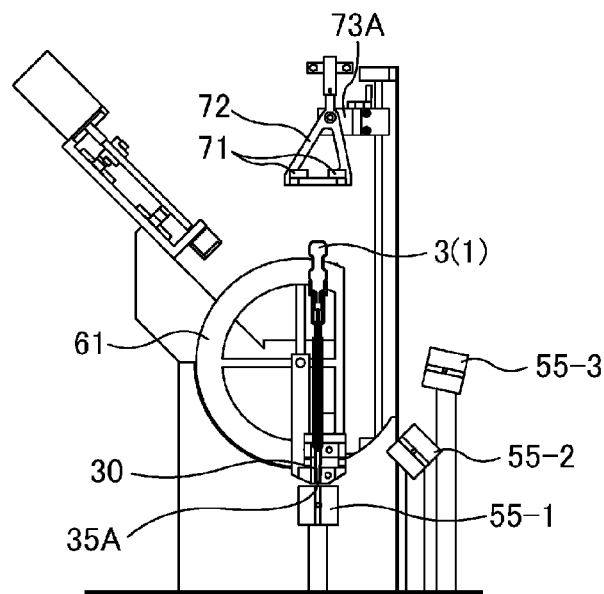
FIGS. 23A and 23B are side views of the main configuration of the PCR apparatus in a fifth embodiment.
Figure 23B:
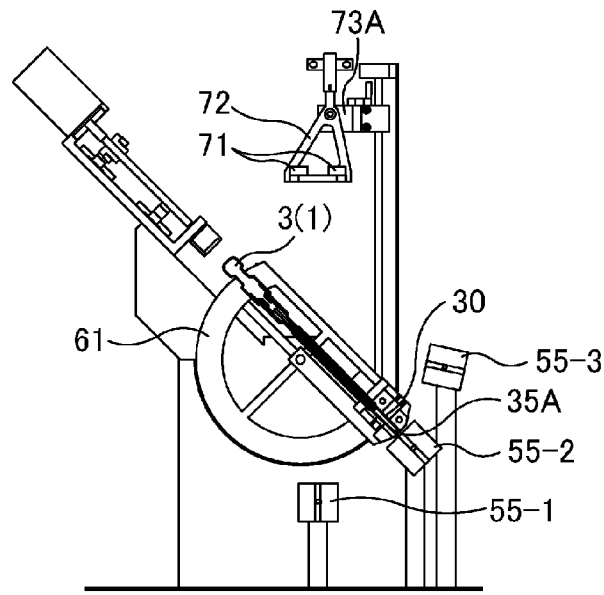

FIGS. 23A and 23B are side views of the main configuration of the PCR apparatus 50 in a fifth embodiment. In FIGS. 23A and 23B, components having functions same as those in the first embodiment are denoted by reference numerals and signs same as those in the first embodiment. As shown in FIG. 23A, a rotating position of the rotating body 61 at the time when a mounting direction of the mounting section 62 is in the up-down direction is set as a reference (0 degree) and a counterclockwise direction viewed from the right is set as a positive direction to show an angle.

In the fifth embodiment, the PCR apparatus 50 includes three fluorescence measuring device 55-1 to 55-3 to be adaptable to multiplex PCR. The three fluorescence measuring devices 55-1 to 55-3 are capable of respectively detecting luminances in different wavelength regions. The fluorescence measuring devices 55-1 to 55-3 are arranged in a range of 0 degree to 90 degrees on a rotation track on which fluorescence measurement for the reaction liquid 47 in the bottom 35A of the PCR container 30 is possible when the rotating body 61 rotates.

Consequently, it is possible to perform track detection in three wavelength regions while the rotating body 61 is rotated. Further, it is possible to provide multiplex PCR for performing luminance detection in a plurality of wavelength regions while rotating the rotating body 61.

Others

The embodiments are provided to facilitate understanding of the invention and not to limitedly interpret the invention. It goes without saying that the invention can be changed and improved without departing from the spirit of the invention and equivalents of the invention are included in the invention.

Concerning the PCR Apparatus

The PCR apparatus 50 changes the posture of the cartridge 1 at the predetermined cycle number and vertically reverses the PCR container 30 in the heat cycle treatment. However, the number of times the posture of the cartridge 1 is changed is not limited to a plurality of times and may be once.

In the PCR apparatus 50, the rotation axis of the rotating body 61 is located closer to the tube 20 than the PCR container 30. However, the position of the rotation axis of the rotating body 61 is not limited to this as long as droplets can move on the inside of the PCR container 30 when the rotating body 61 is rotated and the posture of the cartridge 1 changes.

In the PCR apparatus 50, the fixing section 63, in which the notches are formed, and the insertion hole 64A configures the mounting section 62 for the cartridge 1. However, the PCR apparatus 50 is not limited to this configuration as long as the cartridge 1 can be mounted on the rotating body 61. The mounting section 62 may be structured to fix only the tube side to thereby fix the cartridge 1 to the rotating body 61 or may be structured to fix only the PCR container side to fix the cartridge 1 to the rotating body 61. However, the mounting section 62 needs to be structured to stably fix the cartridge 1 to the rotating body 61 even if the rotating body 61 rotates and the posture of the cartridge 1 changes.

The PCR apparatus 50 includes the high-temperature side heater 65B and the low-temperature side heater 65C as the heaters for PCR. However, the PCR apparatus 50 is not limited to this configuration as long as a temperature gradient can be formed on the inside of the PCR container 30, which is the nucleic acid amplification reaction container. For example, a heater may be provided only on the high temperature side. Alternatively, a heater may be provided on the high temperature side and a cooler may be provided on the low temperature side.

In the PCR apparatus 50, the heaters for PCR (the high-temperature side heater 65B and the low-temperature side heater 65C) are provided in the rotating body 61. However, the heaters for PCR may be provided on the outside of the rotating body 61 as long as a temperature gradient can be formed on the inside of the PCR container 30, which is the nucleic acid amplification reaction container. For example, the PCR apparatus 50 may include, on the outside of the rotating body 61, a first heater for PCR opposed to the PCR container 30 when the rotating body 61 is present in the reference position as shown in FIG. 15A and a second heater for PCR opposed to the PCR container 30 when the rotating body 61 is rotated 180 degrees as shown in FIG. 15C. When the PCR apparatus 50 is configured in this way, it is also possible to form a temperature gradient on the inside of the PCR container 30, which is the nucleic acid amplification reaction container. However, it is desirable that the heaters for PCR are provided in the rotating body 61 because a positional relation between the PCR container 30 of the cartridge 1 and the heaters is maintained irrespective of a rotating position of the rotating body 61.

The PCR apparatus 50 may include only the heaters for PCR (the high-temperature side heater 65B and the low-temperature side heater 65C) without including the heater for elution 65A. However, it is desirable that the PCR apparatus 50 includes the heater for elution 65A because isolation of the nucleic acid from the magnetic beads 7 is accelerated.

The PCR apparatus 50 does not have to include the magnet moving mechanism 70 that moves the magnet along the tube 20. In this case, for example, the operator may hold the magnet and move the magnet along the tube 20. However, it is likely that moving speed or the like of the magnetic beads 7, which are the nucleic acid binding solid-phase carrier, is different depending on the operator. Therefore, it is desirable that the PCR apparatus 50 includes the magnet moving mechanism 70.

The magnet moving mechanism 70 of the PCR apparatus 50 does not have to include the swinging mechanism 75. In this case, although the magnet cannot be swung, the magnet can be moved along the tube 20. Therefore, the magnetic beads 7 bound with the nucleic acid can be moved to a plug including eluate.

The PCR apparatus 50 does not have to include the pressing mechanism 80. In this case, for example, the operator preferably pushes the plunger 10 of the cartridge 1 with a hand. When the plunger 10 is not provided in the cartridge 1, the operator may deform the tank 3 to thereby pressurize the inside of the tank 3 and push out the liquid from the tube 20 to the PCR container 30.

Concerning the Eluate Plug 47A

The eluate plug 47A may be divided into a reverse transcription reaction liquid plug and an eluate plug. In this case, the nucleic acid binding solid-phase carrier washed by the washing solution is moved to the reverse transcription reaction liquid plug to perform the reverse transcription reaction in the reverse transcription reaction liquid plug. This reaction can be performed under conditions suitable for a reverse transcription enzyme in use. For example, it is possible to cause the reverse transcription reaction while keeping RNA bound with a carrier by heating reverse transcription reaction liquid to 30 to 50° C. and preferably 42 to 45° C. and retaining the nucleic acid binding solid-phase carrier in the reverse transcription reaction liquid for a fixed time. A heating method is not particularly limited. However, examples of the heating method include a method of bringing a heat medium such as a heat block into contact with a position corresponding to the reverse transcription reaction liquid plug of the tube 20, a method of using a heat source such as a heater, and a method by electromagnetic heating. The operator can select the retention time as appropriate. However, the nucleic acid binding solid-phase carrier only has to be retained for 10 seconds to 5 minutes and preferably 30 seconds to 1 minute. cDNA synthesized at this stage binds to the solid-phase carrier in a state in which the cDNA remains binding to RNA.

Thereafter, the nucleic acid binding solid-phase carrier is moved to the eluate plug. It is preferable to heat the eluate plug in order to efficiently isolate nucleic acid, in particular, cDNA from the nucleic acid binding solid-phase carrier. A heating method is not particularly limited. A method same as the method used in the heating of the reverse transcription reaction liquid plug can be used. However, a heating temperature only has to be higher than 40° C. and is preferably equal to or higher than 50° C. and more preferably equal to or higher than 60° C. An upper limit of the heating temperature is not particularly limited. However, the upper limit is preferably equal to or lower than 70° C., more preferably equal to or lower than 65° C., still more preferably equal to or lower than 60° C. and most preferably 60° C.

After the nucleic acid is isolated from the nucleic acid binding solid-phase carrier, the nucleic acid binding solid-phase carrier is moved upward from the eluate plug using magnet. The nucleic acid binding solid-phase carrier may be moved to anywhere as long as the nucleic acid binding solid-phase carrier is not mixed in the eluate plug.

By diving the reverse transcription reaction liquid plug and the eluate plug, it is possible to respectively perform the reverse transcription reaction and the nucleic acid elution under high efficiency conditions.

The entire disclosure of Japanese Patent Application No. 2013-156422, filed Jul. 29, 2013 is expressly incorporated by reference herein.

What is claimed is:

1. A nucleic acid amplification reaction apparatus comprising:
   (A) a rotating body configured to mount a nucleic acid amplification reaction container including reaction liquid and oil, wherein the reaction liquid contains a nucleic acid and the oil is phase-separated from the reaction liquid;
   (B) a control section for rotating the rotating body and moving the reaction liquid back and forth between a first region and a second region of the nucleic acid amplification reaction container, when the nucleic acid amplification reaction container is mounted to the rotating body;
   (C) a fluorescence measuring device for performing fluorescence measurement of the reaction liquid in a position along a rotation track of the nucleic acid amplification reaction container at the time when the rotating body rotates, when the nucleic acid amplification reaction container is mounted to the rotating body;
   (D) a first heater that heats the first region of the nucleic acid amplification reaction container when the nucleic acid amplification reaction container is mounted to the rotating body; and (E) a second heater that heats the second region of the nucleic acid amplification reaction container when the nucleic acid amplification reaction container is mounted to the rotating body.

2. The nucleic acid amplification reaction apparatus according to claim 1, wherein the fluorescence measuring device rotates integrally with the rotating body.

3. The nucleic acid amplification reaction apparatus according to claim 1, wherein the fluorescence measuring device moves according to the rotation of the rotating body along the rotation track of the nucleic acid amplification reaction container.

4. The nucleic acid amplification reaction apparatus according to claim 1, wherein a detecting section of the fluorescence measuring device moves, according to the rotation of the rotating body, the position along the rotation track of the nucleic acid amplification reaction container.

5. The nucleic acid amplification reaction apparatus according to claim 4, wherein the fluorescence measuring device includes a fluorescence measuring device main body section, the detecting section, and an optical fiber that connects the fluorescence measuring device main body section and the detecting section.

6. The nucleic acid amplification reaction apparatus according to claim 1, wherein the fluorescence measuring device performs the fluorescence measurement of the reaction liquid when the rotating body is rotating.

7. The nucleic acid amplification reaction apparatus according to claim 1, wherein a plurality of the fluorescence measuring devices are arranged in positions along the rotation track of the nucleic acid amplification reaction container.

* * * * *